United States Patent
Tunc et al.

(10) Patent No.: US 9,445,901 B2
(45) Date of Patent: Sep. 20, 2016

(54) PROSTHESIS WITH SUSTAINED RELEASE ANALGESIC

(76) Inventors: Deger C. Tunc, East Brunswick, NJ (US); Chitranjan S. Ranawat, Alpine, NJ (US); Amar S. Ranawat, New York, NY (US)

(*) Notice: Subject to any disclaimer, the term of this patent is extended or adjusted under 35 U.S.C. 154(b) by 1917 days.

(21) Appl. No.: 10/387,315

(22) Filed: Mar. 12, 2003

(65) Prior Publication Data

US 2004/0180072 A1 Sep. 16, 2004

(51) Int. Cl.
*A61F 2/00* (2006.01)
*A61F 2/30* (2006.01)
(Continued)

(52) U.S. Cl.
CPC ....... *A61F 2/30749* (2013.01); *A61F 2/30721* (2013.01); *A61F 2/30767* (2013.01); *A61F 2/367* (2013.01); *A61F 2/38* (2013.01); *A61L 27/18* (2013.01); *A61L 27/54* (2013.01); *A61F 2/28* (2013.01); *A61F 2/32* (2013.01); *A61F 2/34* (2013.01); *A61F 2/36* (2013.01); *A61F 2/389* (2013.01); *A61F 2/3859* (2013.01); *A61F 2002/30062* (2013.01); *A61F 2002/30133* (2013.01); *A61F 2002/30448* (2013.01); *A61F 2002/30604* (2013.01); *A61F 2002/30677* (2013.01); *A61F 2002/30733* (2013.01); *A61F 2002/30795* (2013.01); *A61F 2002/30827* (2013.01); *A61F 2002/30878* (2013.01); *A61F 2002/3403* (2013.01); *A61F 2002/3443* (2013.01); *A61F 2002/365* (2013.01); *A61F 2002/3611* (2013.01); *A61F 2002/3625* (2013.01); *A61F 2002/3694* (2013.01); *A61F 2210/0004* (2013.01); *A61F 2220/005* (2013.01); *A61F 2230/0015* (2013.01);

(Continued)

(58) Field of Classification Search
CPC .............. A61F 2/30; A61F 2/28; A61F 2/32; A61F 2/42; A61F 2210/0004
USPC ........ 424/424–246, 424–446; 623/16, 11.11, 623/13.12, 13.18, 16.11, 17.12, 623/18.11–20.11, 23.15, 23.39, 23.44; 604/175, 891.1, 93.1
See application file for complete search history.

(56) References Cited

U.S. PATENT DOCUMENTS

| | | |
|---|---|---|
| 3,773,919 A | 11/1973 | Boswell et al. |
| 3,991,766 A | 11/1976 | Schmitt et al. |

(Continued)

FOREIGN PATENT DOCUMENTS

| | | | |
|---|---|---|---|
| EP | 0 523 926 A1 | * | 1/1993 |
| EP | 0 523 926 A2 | | 1/1993 |

(Continued)

OTHER PUBLICATIONS

"Pipeline," Innocoll Inc. webpage, http://www.innocall-tech.com/pipeline_main.html, date unknown, printed Jul. 14, 2006.

*Primary Examiner* — Micah-Paul Young
(74) *Attorney, Agent, or Firm* — Baker Botts, LLP

(57) ABSTRACT

A device for releasing a therapeutic agent in the body space in the form of a prosthetic joint implant having a first portion such as a stemmed portion for contacting bone tissue in an intramedullary canal of a long bone. The implant has a second portion which extends into the body space such as a joint space. The joint component contains a reservoir filled with a bioabsorbable/resorbable polymer which includes a therapeutic agent. The reservoir is open or in contact with the joint space as the body fluid diffuses in and out of the polymeric device it carries the drug into the joint space.

37 Claims, 23 Drawing Sheets

(51) Int. Cl.
*A61F 2/38* (2006.01)
*A61L 27/18* (2006.01)
*A61L 27/54* (2006.01)
*A61F 2/28* (2006.01)
*A61F 2/32* (2006.01)
*A61F 2/34* (2006.01)
*A61F 2/36* (2006.01)

(52) U.S. Cl.
CPC . *A61F 2310/0097* (2013.01); *A61L 2300/402* (2013.01); *A61L 2300/406* (2013.01); *A61L 2300/602* (2013.01)

(56) References Cited

U.S. PATENT DOCUMENTS

| | | | |
|---|---|---|---|
| 4,293,539 A | 10/1981 | Ludwig et al. | |
| 4,419,340 A | 12/1983 | Yolles | |
| 4,523,591 A | 6/1985 | Kaplan et al. | |
| 4,550,449 A | 11/1985 | Tunc | |
| 4,563,489 A | 1/1986 | Urist | |
| 4,622,219 A | 11/1986 | Haynes | |
| 4,637,905 A | 1/1987 | Gardner | |
| 4,719,246 A | 1/1988 | Murdoch et al. | |
| 4,725,442 A | 2/1988 | Haynes | |
| 4,886,870 A | 12/1989 | D'Amore et al. | |
| 4,919,666 A | 4/1990 | Buchhorn et al. | |
| 4,938,763 A | 7/1990 | Dunn et al. | |
| 5,061,492 A | 10/1991 | Okada et al. | |
| 5,133,771 A * | 7/1992 | Duncan et al. | 623/23.2 |
| 5,188,837 A | 2/1993 | Domb | |
| 5,246,461 A * | 9/1993 | Tepic | 623/23.32 |
| 5,344,654 A | 9/1994 | Rueger et al. | |
| 5,378,475 A | 1/1995 | Smith et al. | |
| 5,512,055 A | 4/1996 | Domb et al. | |
| 5,567,431 A | 10/1996 | Vert et al. | |
| 5,599,552 A * | 2/1997 | Dunn et al. | 424/423 |
| 5,618,563 A | 4/1997 | Berde et al. | |
| 5,681,289 A * | 10/1997 | Wilcox et al. | 604/175 |
| 5,700,901 A | 12/1997 | Hurst et al. | |
| 5,707,647 A * | 1/1998 | Dunn et al. | 424/443 |
| 5,717,030 A * | 2/1998 | Dunn et al. | 523/111 |
| 5,773,019 A | 6/1998 | Ashton et al. | |
| 5,836,935 A | 11/1998 | Ashton et al. | |
| 5,837,752 A | 11/1998 | Shastri et al. | |
| 5,871,484 A | 2/1999 | Spievack et al. | |
| 5,876,446 A | 3/1999 | Agrawal et al. | |
| 5,876,452 A * | 3/1999 | Athanasiou et al. | 623/23.72 |
| 5,895,375 A | 4/1999 | Wilcox et al. | |
| 5,902,598 A | 5/1999 | Chen et al. | |
| 5,919,473 A | 7/1999 | Elkhoury | |
| 5,935,594 A | 8/1999 | Ringeisen et al. | |
| 5,942,241 A | 8/1999 | Chasin et al. | |
| 5,945,128 A * | 8/1999 | Deghenghi | 424/501 |
| 5,947,893 A | 9/1999 | Agrawal et al. | |
| 5,958,430 A | 9/1999 | Campbell et al. | |
| 5,980,927 A | 11/1999 | Nelson et al. | |
| 6,001,386 A | 12/1999 | Ashton et al. | |
| 6,007,580 A * | 12/1999 | Lehto et al. | 623/21.11 |
| 6,013,853 A | 1/2000 | Athanasiou et al. | |
| 6,051,576 A | 4/2000 | Ashton et al. | |
| 6,059,817 A | 5/2000 | Bonutti et al. | |
| 6,071,982 A * | 6/2000 | Wise et al. | 523/113 |
| 6,206,883 B1 | 3/2001 | Tunc | |
| 6,214,370 B1 | 4/2001 | Nelson et al. | |
| 6,214,387 B1 | 4/2001 | Berde et al. | |
| 6,217,895 B1 | 4/2001 | Guo et al. | |
| 6,238,702 B1 | 5/2001 | Berde et al. | |
| 6,248,345 B1 | 6/2001 | Goldenheim et al. | |
| 6,281,256 B1 * | 8/2001 | Harris et al. | 521/51 |
| 6,328,988 B1 | 12/2001 | Uhrich | |
| 6,355,705 B1 | 3/2002 | Bond et al. | |
| 6,365,146 B1 | 4/2002 | Uhrich | |
| 6,375,972 B1 | 4/2002 | Guo et al. | |
| 6,391,336 B1 | 5/2002 | Royer | |
| 6,451,335 B1 * | 9/2002 | Goldenheim et al. | 424/426 |
| 6,468,519 B1 | 10/2002 | Uhrich | |
| 6,514,286 B1 | 2/2003 | Leatherbury et al. | |
| 6,531,154 B1 | 3/2003 | Mathiowitz et al. | |
| 6,544,266 B1 | 4/2003 | Roger et al. | |
| 2002/0106345 A1 | 8/2002 | Uhrich et al. | |
| 2002/0169162 A1 * | 11/2002 | Smith et al. | 514/248 |
| 2004/0013703 A1 | 1/2004 | Ralph et al. | |

FOREIGN PATENT DOCUMENTS

| | | | |
|---|---|---|---|
| EP | 0 523 926 A2 * | 1/1993 | A61F 2/30 |
| EP | 0523926 | 1/1993 | |
| JP | 08146449 A1 * | 6/1996 | A61K 9/08 |
| WO | WO 94/05265 | 3/1994 | |
| WO | WO 98/34653 | 8/1998 | |
| WO | WO 02/36175 | 5/2002 | |
| WO | WO-02/36175 A2 | 5/2002 | |
| WO | WO 03/092514 | 11/2003 | |
| WO | WO-03/092514 A1 | 11/2003 | |

* cited by examiner

Magn ⊢————⊣ 100 μm
200x  479-46-1

Magn ⊢————⊣ 20 μm
1000x  479-46-1

Magn ⊢———⊣ 100 μm
200x  479-47-4

Magn ⊢———⊣ 20 μm
1000x  479-47-4

Magn ⊢────────⊣ 100 μm
200x 479-87-1

Magn ⊢────────⊣ 20 μm
1000x 479-87-1

Magn ⊢————⊣ 100 μm
200x  479-87-2

Magn ⊢————⊣ 20 μm
1000x  479-87-2

PROSTHESIS WITH SUSTAINED RELEASE ANALGESIC

BACKGROUND OF THE INVENTION

The present invention is related to sustained release of locally active agents and/or diagnostic agents from prosthetic implants into joint spaces or into other body spaces. In particular embodiments, the invention provides structures and compositions for the administration of local anesthetics in the joint areas in patients in need thereof.

Treatment of joint pain and infection after implantation of a joint prosthesis has hereto been based on the use of systemic treatment with antibodies and steroidal and non-steroidal anti-inflammatory agents and analgesics as well as localized injection of steroidal anti-inflammatories, e.g., intra articular injection, and local anesthetics, either intra articular or proximal in the innervation of the painful joint. Localized treatment is generally preferred over systemic treatment, particularly when treating severe, localized joint pain, in order to avoid the untoward systemic effects associated with the high levels of both steroidal and nonsteroidal anti-inflammatory agents otherwise required. Local anesthetics alone have previously been injected into joint spaces to relieve pain, with mixed results.

Local anesthetics act by producing a loss of sensation in the localized area of administration in the body. The mechanism by which local anesthetics induce their effect, while not having been determined definitively, is generally thought to be based upon the ability to interfere with the initiation and transmission of the nerve impulse. The duration of action of a local anesthetic is proportional to the time during which it is in actual contact with the nervous tissues. Consequently, devices for formulations that maintain localization of the drug at the nerve greatly prolong anesthesia.

Local anesthetics are potentially toxic, yet must remain at the site long enough to allow sufficient time for the localized pain to subside. Therefore, it is of great importance that factors such as the choice of drug, concentration of drug, and rate and site of administration of drug be taken into consideration when contemplating their use.

Different devices and formulations are known in the art for administration of local anesthetics. For example, local anesthetics can be delivered in solution or suspension by means of injection, infusion, infiltration, irrigation, topically and the like. Injection or infusion can be carried out acutely, or if prolonged local effects are desired, localized anesthetic agents can be administered continuously by means of a gravity drip or infusion pump. Thus, local anesthetics such as bupivacaine have been administered by continuous infusion, e.g., for prolonged epidural or intrathecal administration.

Sustained release carriers for local anesthetics have been described. For example, U.S. Pat. Nos. 4,725,442 and 4,622,219 (Haynes) relate to methoxyflurane-containing microdroplets coated with a phospholipid prepared by sonication, which are suitable for intradermal or intravenous injection into a patient for inducing local anesthesia. Such microdroplets are said to cause long-term local anesthesia when injected intradermally, giving a duration of anesthesia considerably longer than the longest acting conventional local anesthetic (bupivacaine).

U.S. Pat. No. 5,188,837 (Domb) relates to a microsuspension system containing lipospheres having a layer of a phospholipid imbedded on their surface. The core of the liposphere is a solid substance to be delivered, or the substance to be delivered is dispersed in an inert vehicle. The substance to be delivered can be, e.g., nonsteroidal anti-inflammatory compounds, local anesthetics, water insoluble chemotherapeutic agents and steroids.

Other formulations directed to injectable microcapsules, etc. are known. For example, U.S. Pat. No. 5,061,492 describes prolonged release microcapsules of a water soluble drug in a bioabsorbable/resorbable polymer matrix which is composed of a copolymer of glycolic acid and a lactic acid. The microcapsules are prepared as an injectable preparation in a pharmaceutically acceptable vehicle. The particles of water soluble drug are retained in a drug-retaining substance dispersed in a matrix of the lactic/glycolic acid copolymer in a ratio of 100/1 to 50/50 and an average molecular weight of 5,000-200,000. The injectable preparation is made by preparing a water-in-oil emulsion of an aqueous layer of drug and drug retaining substance and an oil layer of the polymer, thickening and then water-drying.

U.S. Pat. No. 4,938,763 (Dunn et al.) is related to a bioabsorbable/resorbable polymer for use in providing syringeable, in-situ forming, solid bioabsorbable/resorbable implants for animals. In one aspect of this reference, a thermosetting system is utilized which utilizes copolymers which may be derived from polylactides and/or polyglycolides, combinations and mixtures of these and other polymers.

U.S. Pat. No. 4,293,539 (Ludwig et al.) relates to controlled release formulations comprised of a microbial agent dispersed throughout a copolymer derived from lactic acid and glycolic acid. The copolymer is derived from 60-95% lactic acid and 40-5% glycolic acid by weight, and has a molecular weight of 6,000-35,000. An effective amount of the copolymeric formulation is administered by subcutaneous or intramuscular administration.

WO 94/05265 describes improved bioabsorbable/resorbable sustained release systems consisting of a polymeric matrix incorporating a local anesthetic for the prolonged administration of the local anesthetic agent. The devices are selected on the basis of their degradation profiles; release of the topical anesthetic in a controlled manner over the period of preferably two weeks and degradation of the polymer in vivo with a half-life of less than six months, more preferably two months, to avoid localized inflammation. The disclosure states that an anti-inflammatory can be incorporated into the polymer with the local anesthetic to reduce encapsulation for optimal access of drug to its site of action. The anti-inflammatories that are said to be useful include steroids such as dexamethasone, cortisone, prednisone, and others routinely administered orally or by injection.

A relatively long-acting anesthetic, bupivacaine hydrochloride, is commercially available as Marcaine® Hydrochloride in sterile isotonic solutions with and without epinephrine (as bitartrate) 1:200,000 for injection via local infiltration, peripheral nerve block, and caudal and lumbar epidural blocks. After injection of Marcaine for caudal, epidural or peripheral nerve block in man, peak levels of bupivacine in the blood are reached in 30 to 45 minutes, followed by a decline to insignificant levels during the next three to six hours.

In addition, polymer microspheres have long been used for both medical and non-medical applications where sustained release of an agent of interest is desired. Nevertheless, prior to the present invention, the need for an effective method and formulation for delivering pain relief and other pharmaceutical or diagnostic treatments to the joints space has remained unmet. Further, the need for an effective method and formulation for delivering pain relief and other

SUMMARY OF THE INVENTION

It is an object of the present invention to provide a bioabsorbable/resorbable sustained release dosage form for providing prolonged administration of an active agent for the treatment of joint pain or other joint conditions in humans and animals.

More particularly, it is an object of the invention to provide a local anesthetic in a biocompatible, bioabsorbable/resorbable sustained release form located in a body cavity or attached to an implanted medical device.

It is a further object of the present invention to provide a method for prolonging the effect of a local anesthetic agent in joints and/or body spaces and cavities and to further provide a prolonged and beneficial anti-inflammatory effect.

It is still a further object of the present invention to provide a biocompatible, bioabsorbable/resorbable controlled release dosage form for providing prolonged local anesthetic treatment within body spaces in humans and animals.

It is an additional object of the invention to provide a prosthetic joint implant capable of releasing therapeutic agents such as pain relievers into a joint space.

It is still an additional object to provide a prosthetic joint component including a reservoir formed therein for releasing an analgesic into the joint space for a predetermined period of time after the prosthesis has been implanted.

It is yet an additional object of the invention to provide prosthetic hip and knee implants having portions of the implant extending into the joint space, which portions include bioabsorbable/resorbable polymers having included therein an analgesic or other therapeutic agent.

These and other objects of the invention are provided for in a device for releasing the therapeutic agent in a body space wherein the device has a first portion for directly contacting tissue and a second portion extending into a joint space. The second portion includes a reservoir in the form of a recess or cavity therein open to or extending into the joint space. The recess forming the reservoir contains the bioabsorbable/resorbable polymer combined with the analgesic or other therapeutic agent. As water molecules diffuse into the device and dissolve the drug molecules in the device, the analgesic or other therapeutic agent is released into the joint space. As the polymer degrades, the rate of release of the drug increases. A useful polymer is disclosed in U.S. Pat. No. 4,550,449 which issued to the present inventor, the teachings of which are incorporated herein by reference.

In addition, the bioabsorbable/resorbable polymer may be porous with the pores filled or coated with the therapeutic agent. In this case, the therapeutic agent is released, at least in part, independently of the degradation of the polymer. The loaded polymeric delivery device could of course be used independently of the prosthesis, i.e., formed into rods, films or pouches and placed in the joint.

The therapeutic agent may be an analgesic or an antibiotic or a combination thereof. The analgesic may be selected from the group consisting of bupivacaine, ropivacaine, dibucaine, etidocaine, tetracaine, lidocaine, xylocalne and combinations thereof and/or salts and derivatives thereof, either alone or in combination. The analgesic may also be derived from opiates.

The antibiotics used may be selected from the group consisting of sulfisoxazole, penicillin, ampicillin, sephalosporins, gentamicin, erythromycin, tetracylines and derivatives, salts and mixtures thereof. The above list is by way of example only and not a limitation on the numerous analgesics and antibiotics or other therapeutic agents which may be used. For example, capable anti-inflammatory agents, bisphosonates such as Fossamax® may be used with the present invention.

In general, the therapeutic agent is between 1% and 90% by weight of the bioresorbable polymer. The polymer may be placed in a reservoir in the joint component. The reservoir may be formed within a stem portion in a cavity completely surrounded by the metal stem with an opening at an end of the implant open to the joint space. The opening may be in a portion of the joint component which extends beyond the bone and into a joint space. A passageway may extend from the stem portion having the reservoir to an external surface of the implant within the joint space to allow joint fluid to contact and diffuse into and out of the bioresorbable polymer to release the drug molecules. Alternately, the therapeutic agent may be formed as a coating around non-load bearing surfaces of the implant, which surfaces extend into or are exposed to the joint space.

In one aspect, the sustained release material comprises a polymer such as polyanhyrdrides, copolymers of lactic acid and glycolic acid, poly(lactic) acid, poly(glycolic) acid, polyesters, polyorthoesters, proteins, polysaccharides and/or combinations thereof. Preferably, the polymers are bioabsorbable/resorbable so that manual removal is avoided. Such a polymer is taught in U.S. Pat. No. 4,550,449. The polymer of the present invention is preferably a terpolymer of L-lactide, D-lactide, and glycolide. However, additional compatible polymeric repeating units may be included in the materials of the present invention. Such polymeric repeating units, which will preferably be included in amounts of less than about 5 molar percent, more preferably less than about 2.5 molar percent, can be made by including the following monomers in the reactants, alone or in combination:

alpha-hydroxy-alpha-ethylbutyric acid;
alpha-hydroxy-beta-methylvaleric acid;
alpha-hydroxyacetic acid;
alpha-hydroxybutyric acid;
alpha-hydroxycaporic acid;
alpha-hydroxydecanoic acid;
alpha-hydroxyheptanoic acid;
alpha-hydroxyisobutyric acid;
alpha-hydroxyisocaproic acid;
alpha-hydroxyisovaleric acid;
alpha-hydroxymyristic acid;
alpha-hydroxyoctanoic acid;
alpha-hydroxystearic acid;
alpha-hydroxyvaleric acid;
beta-butyrolactone;
beta-propiolactide;
gamma-butyrolactone;
pivalolactone; and
tetramethylglycolide.

The sustained release formulation can contain any quantity of local anesthetic compatible with the selected polymer formulation. Preferably, the local anesthetic is incorporated into the sustained release material at a percent loading of 10% to 60% by weight. Any local anesthetic known to the art may be employed. Preferred local anesthetics include bupivacaine, ropivacaine, dibucaine, procaine, chloroprocaine, mepivicaine, cinchocaine, prilocalne, cocaine, benzocaine, butamben and morphine, etidocaine, tetracaine, lidocaine, xylocalne, mixtures thereof, and/or salts and derivatives thereof. As examples of the antibiotics, may be mentioned gentamicin, dibekacin, kanendomycin, lividomycin, tobramycin, amikacin, fradiomycin, sisomicin, tetracycline, hydrochloride, oxytetracycline, hydrochloride, rolitetracycline, doxycycline hydrochloride, ampicillin, piperacillin, ticarcillin, cephalothin, cephaloridine, cefotiam, cefsulodin, cefinenoxime, cefinetazole, cefazolin, cefotaxime, cefoperazone, ceftizoxime, moxolactam, latamoxef, thienamycin, sulfazecin, azthreonam and a combination thereof.

The controlled release formulations and methods of the invention may be used in conjunction with any bioabsorbable/resorbable system for application, infiltration, implantation, insertion, or injection into the reservoir known in the art, including but not limited to microparticles, e.g., microspheres or microcapsules, gels, pastes, rods, pellets, plates or fibers, and the like (generically referred to as "substrates"). The bioabsorbable/resorbable system may be a polylactide polymer, either alone or a copolymer with polyglycolide. The bioabsorbable/resorbable polymer may be the terpolymer disclosed in U.S. Pat. No. 6,206,883 issued to the inventor of the present application, the teachings of which are incorporated herein by reference.

As used herein, the terms, "sustained release" and "controlled release" are well understood in the art and are intended to be interchangeable.

As used herein, the terms "local anesthetic agent" or "local anesthetic" means any drug which provides local numbness and/or analgesia. The term also includes, but is not limited to, any drug which, when locally administered, e.g., topically or by infiltration or injection, provides localized full or partial inhibition of sensory perception and/or motor function. Under either definition, the localized condition so induced is also referred to herein as "local anesthesia." Local anesthetic agents which can be used include, simply by way of example, bupivacaine, ropivacaine, dibucaine, procaine, chloroprocaine, prilocalne, mepivacaine, etidocaine, tetracaine, lidocaine, and xylocalne, as well as anesthetically active derivatives, analogs and mixtures thereof. The local anesthetic can be in the form of a salt, for example, the hydrochloride, bromide, acetate, citrate, carbonate or sulfate. More preferably, the local anesthetic agent is in the form of a free base. The free base provides a slower initial release and avoids an early "dumping" of the local anesthetic at the release site. Preferred local anesthetic agents include, e.g., bupivacaine. The term "local anesthetic" may also encompass, pursuant to the definitions provided herein, a drug of a different class than those traditionally associate with local anesthetic properties, including but not limited to morphine, fentanyl, and agents which, for example, can provide regional blockade of nociceptive pathways (afferent and/or efferent).

DETAILED DESCRIPTION OF THE PREFERRED EMBODIMENTS

Figure 1:
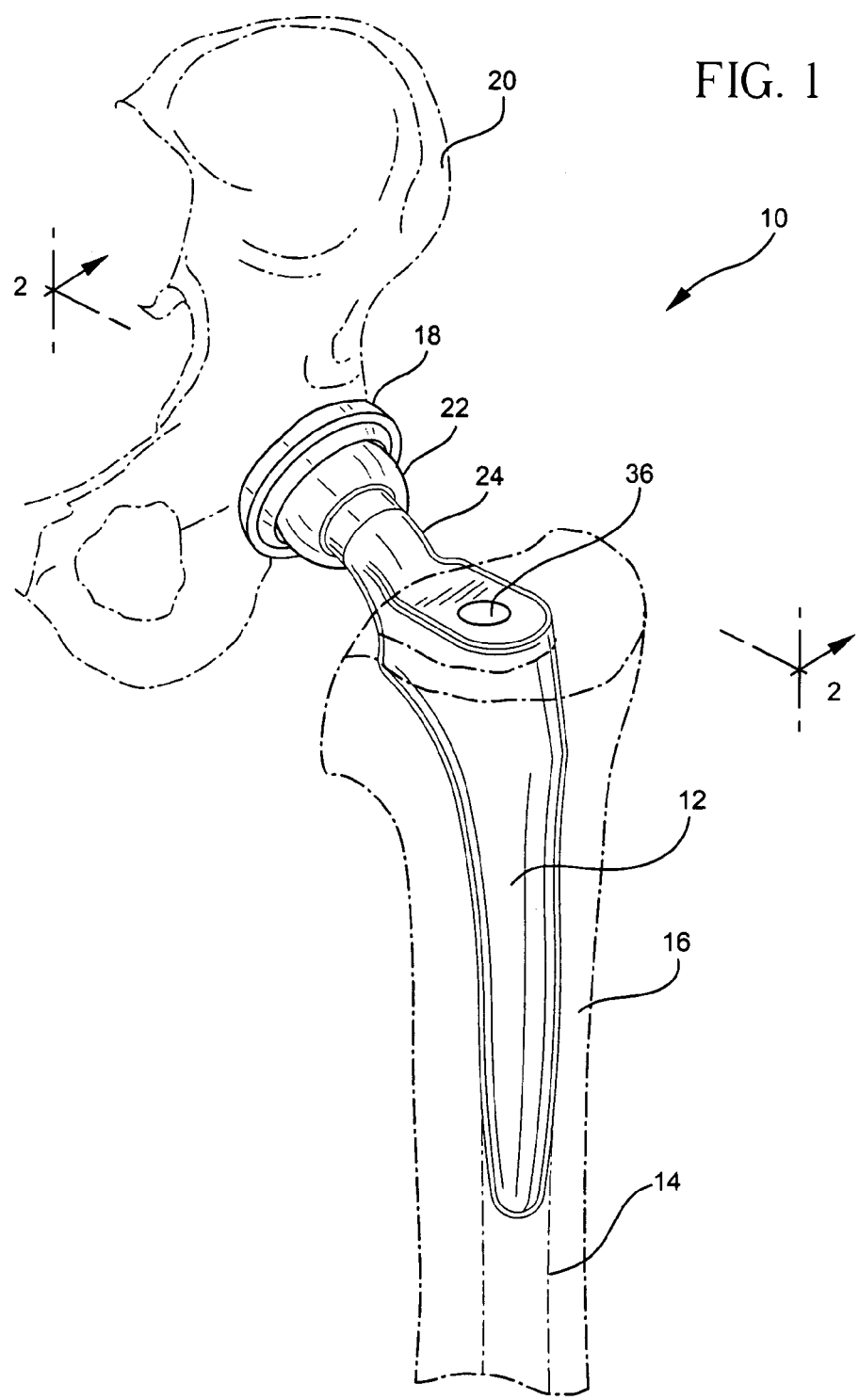
FIG. 1 is an isometric view of a joint component of the present invention implanted within the medullary canal of a femur.

Referring to FIG. 1, there is shown a hip joint component generally denoted as 10 having a femoral component 12 implanted in the medullary canal 14 of a femur 16. Also shown is the acetabular prosthetic component 18 implanted within pelvis 20. A prosthetic femoral head or ball 22 is mounted on the proximal end 24 of femoral component 12.

Figure 2:
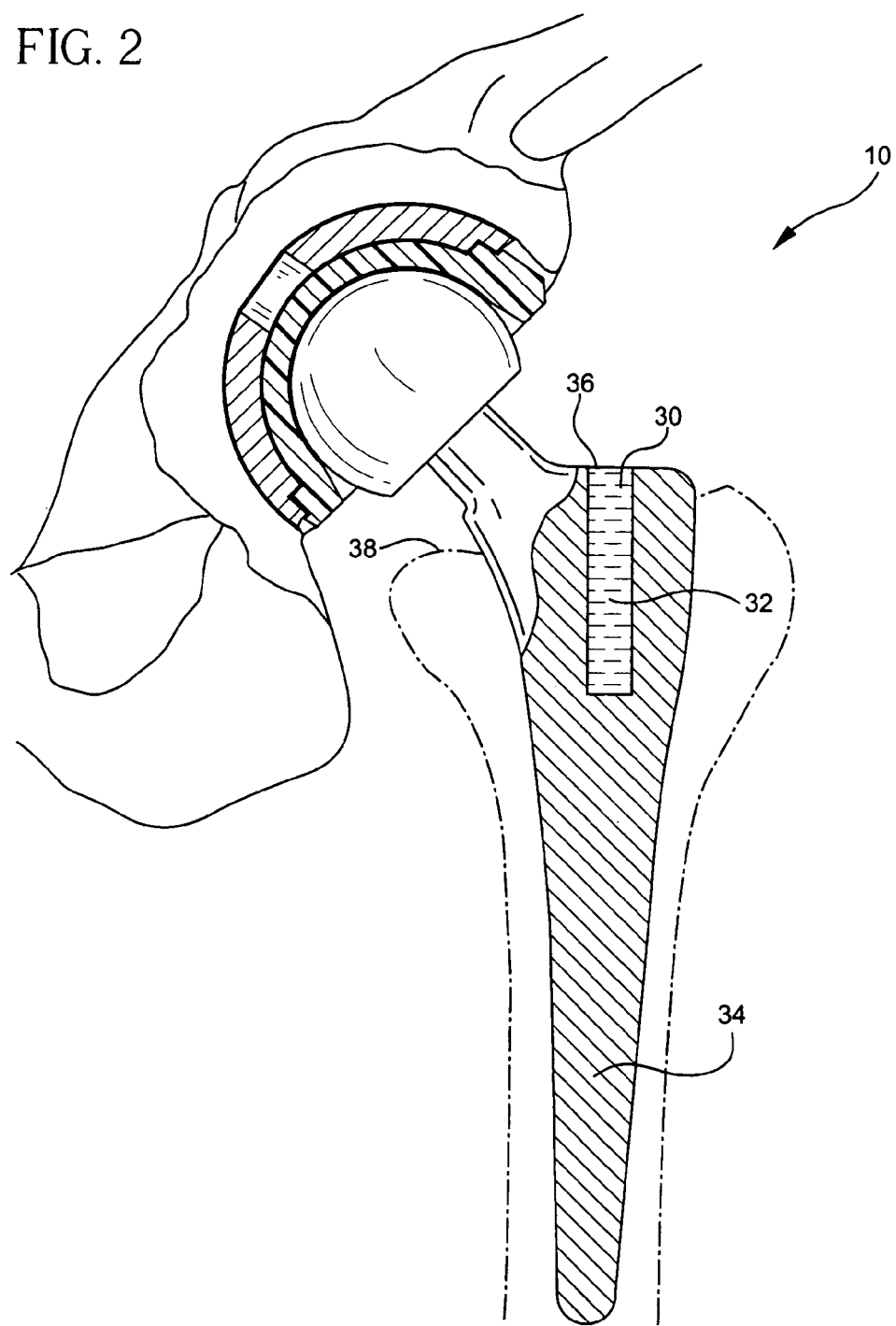
FIG. 2 is a cross-sectional view of the prosthetic joint implant shown in FIG. 1 along lines 2-2.

Referring to FIG. 2, there is shown a cross-sectional view of the femoral joint component 10 showing a reservoir 30 formed in stem 34. In the preferred embodiment, reservoir 30 is a cylindrical bore formed within stem 34 having an opening 36. Opening 36 communicates with the joint space 38. Reservoir 30 is filled with a bioabsorbable/resorbable material 32 which includes a therapeutic agent such as an analgesic or antibiotic. Typically the bore is about 0.25 inches.

Figure 3:
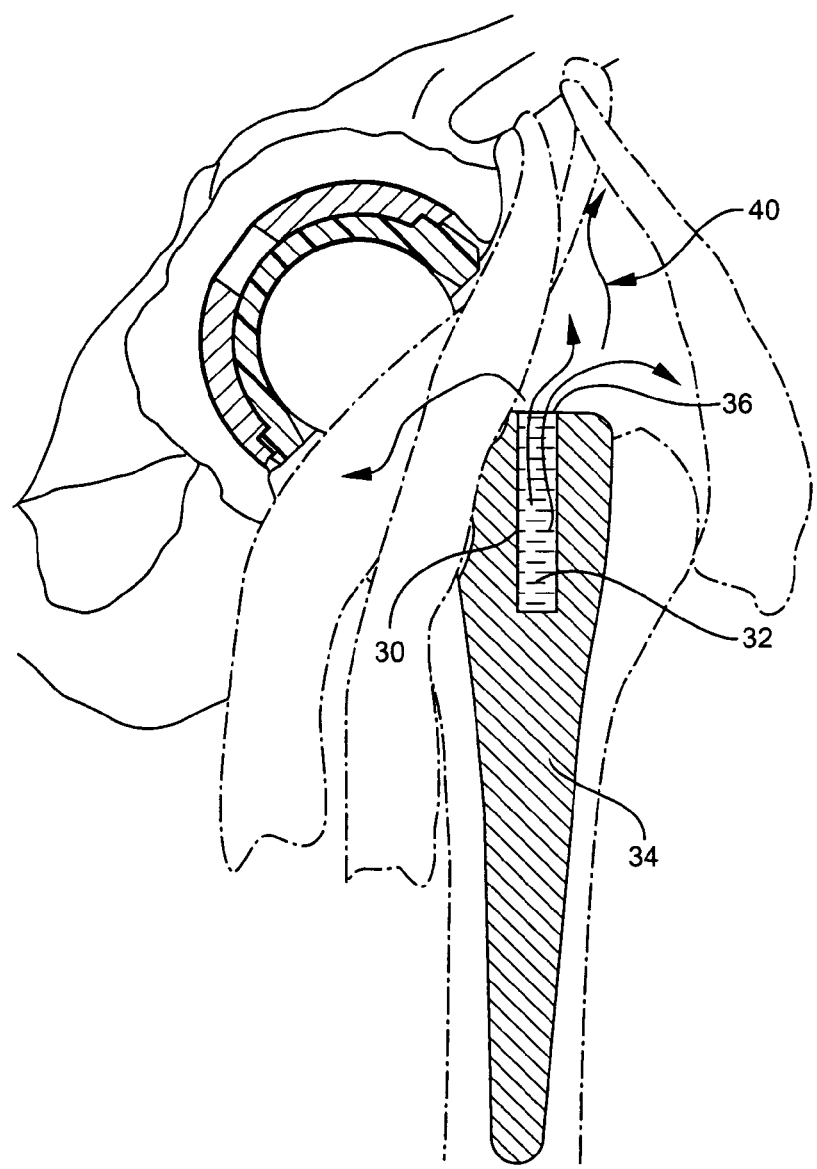
FIG. 3 is a cross-sectional view of the joint component shown in FIG. 2 after implantation depicting the therapeutic agent exiting the reservoir in the joint component and then flowing into the joint space.

Referring to FIG. 3, there is shown hip stem 34 eluting analgesic, or antibiotic or other therapeutic agent via the degradation of the bioresorbable polymer 32. As can be seen, the antibiotic or analgesic generally denoted by arrows 40 elutes through the proximal opening 36 within stem 34. This eluting may be independent of the degradation time of the resorbable implant which may be up to two months while the therapeutic agent may be totally released in a matter of days.

Figure 4:
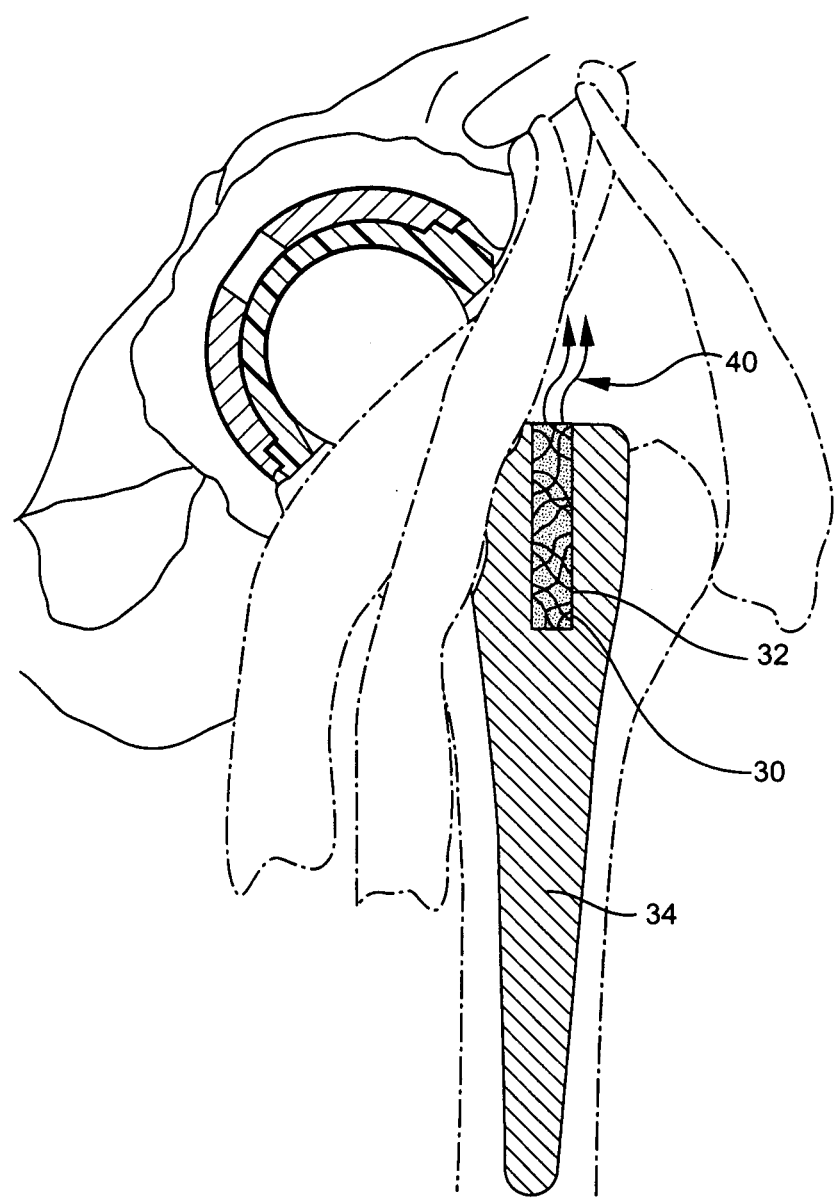
FIG. 4 is a cross-sectional view of the joint component shown in FIG. 3 with the bioresorbable material partially eroded by joint fluids.

Referring to FIG. 4, there is shown stem 34 with the bioabsorbable material 32 partially absorbed from reservoir 30. The two shorter arrows 40 of FIG. 4 are meant to convey that the amount of antibiotic or analgesic released by the resorbable polymer decreases over time. Degradation time as well as eluting time can be controlled by the porosity of the material as well as the size of the opening 36 exposed to the joint fluid.

Figure 5:
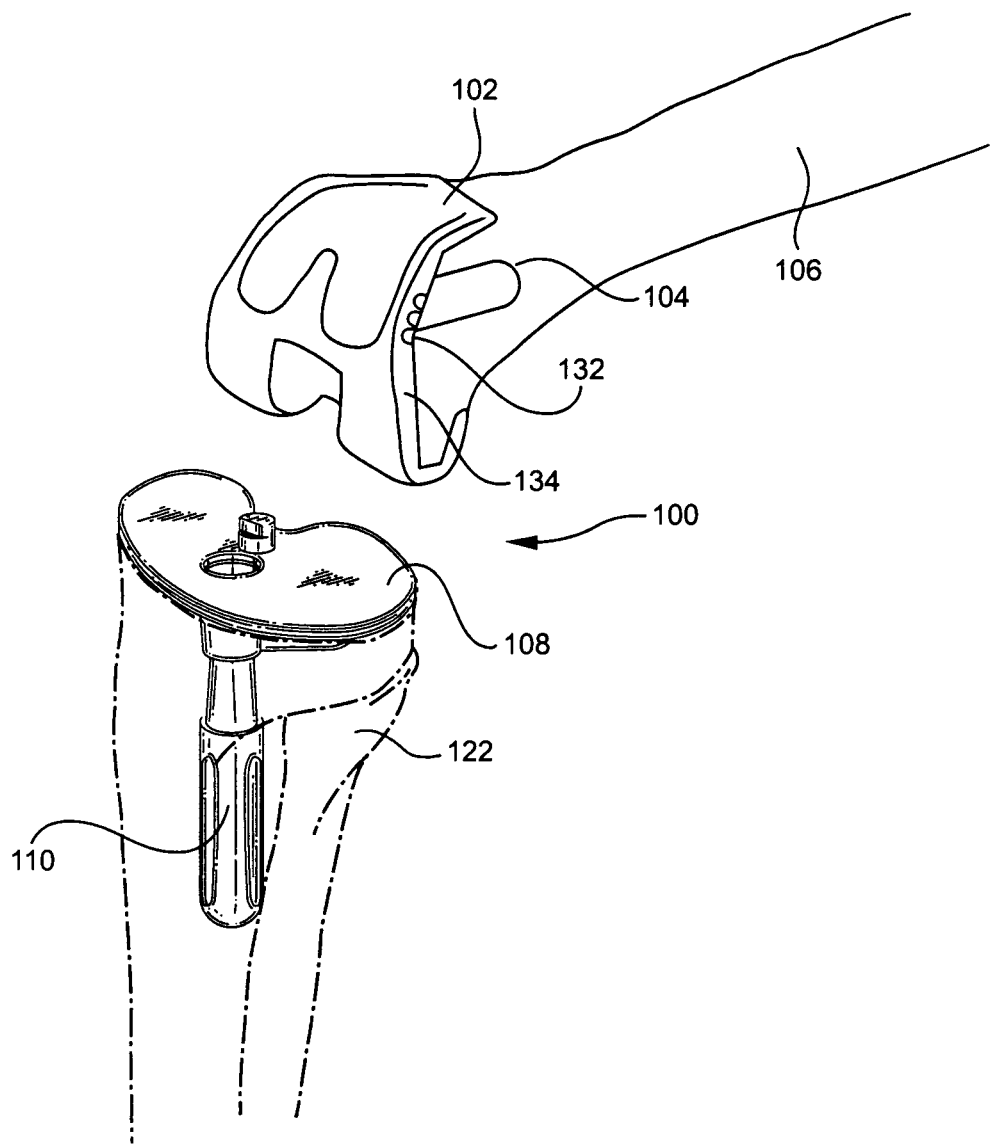
FIG. 5 is an isometric view of a prosthetic knee implant, including femoral and tibial components.

Referring to FIG. 5, there is shown a prosthetic knee implant generally denoted as 100 which includes a femoral component 102 having stem 104 for insertion into the distal medullary canal of the femur 106 and a tibial component 108 which includes a stem 110 for insertion into the medullary canal of the tibia 112.

Figure 6:
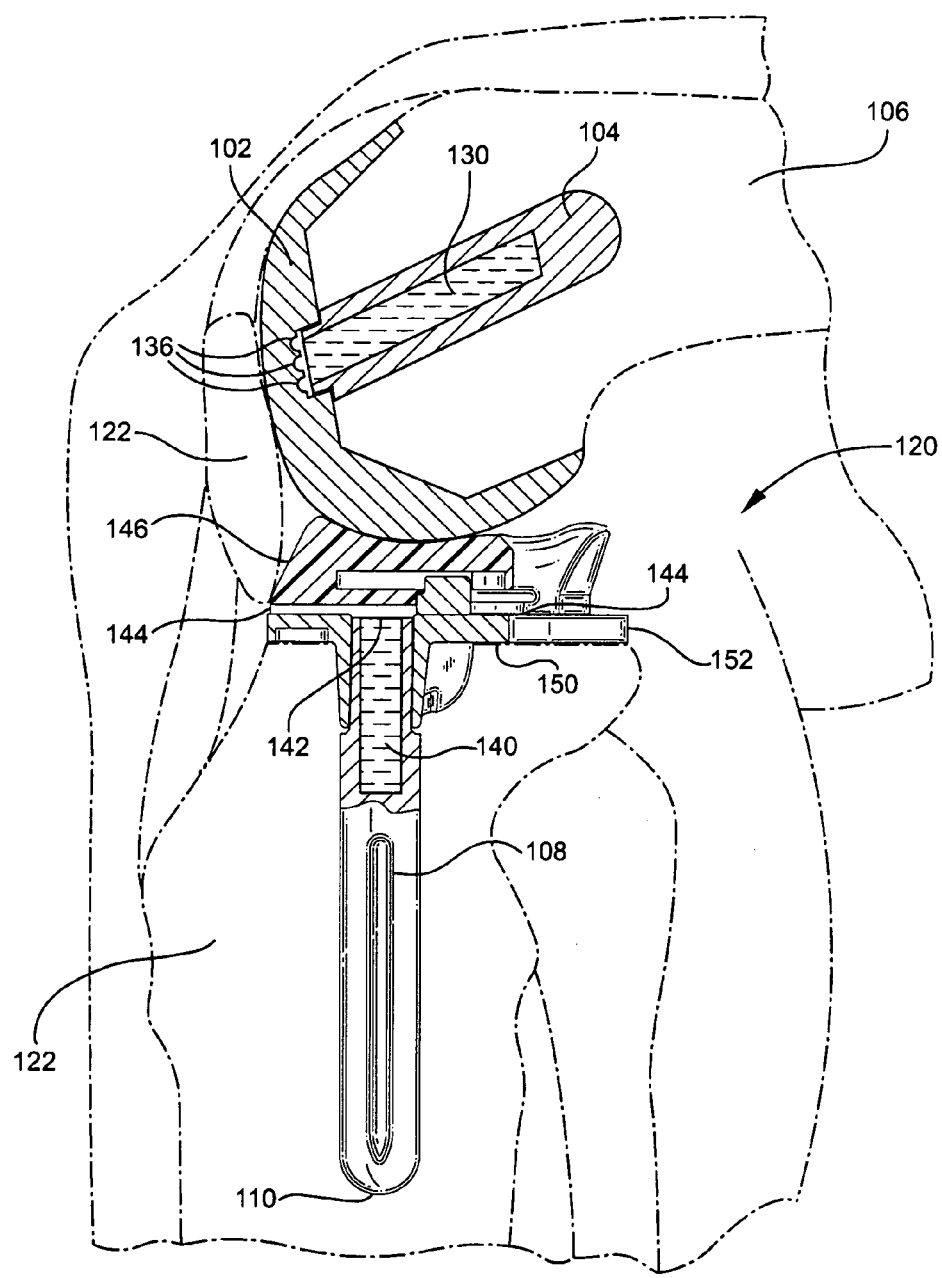
FIG. 6 is a cross-sectional view of a joint component shown in FIG. 5, showing reservoirs for a bioabsorbable/resorbable polymer having a therapeutic agent therein.

Referring to FIG. 6, there is shown a cross-sectional view of the knee prosthesis 100, including a joint space 120.

Shown in phantom is a patella 122 which rides in the patella groove of the femoral component 102. The preferred stem 104 of femoral component 102 includes a reservoir 130 which communicates with the joint space 120 via a plurality of grooves 132. In the preferred embodiment, one or more grooves 132 extend in the medial-lateral direction and intersect the medial and lateral external surface 134 of femoral component 102 (see FIG. 5). Consequently, joint fluid can enter through the medial and lateral openings of grooves 132 and communicate with the reservoir 130. As described above, reservoir 130 includes the bioresorbable polymer having an analgesic or antibiotic or other therapeutic agent therein.

Tibial component 108 also includes a reservoir 140 in stem 110. The reservoir 140 has an open end 142 which leads to a passage 144 which, in turn, leads to the joint space 120. In the preferred embodiment, the passageway is formed in the polyethylene bearing component 146.

Figure 7:
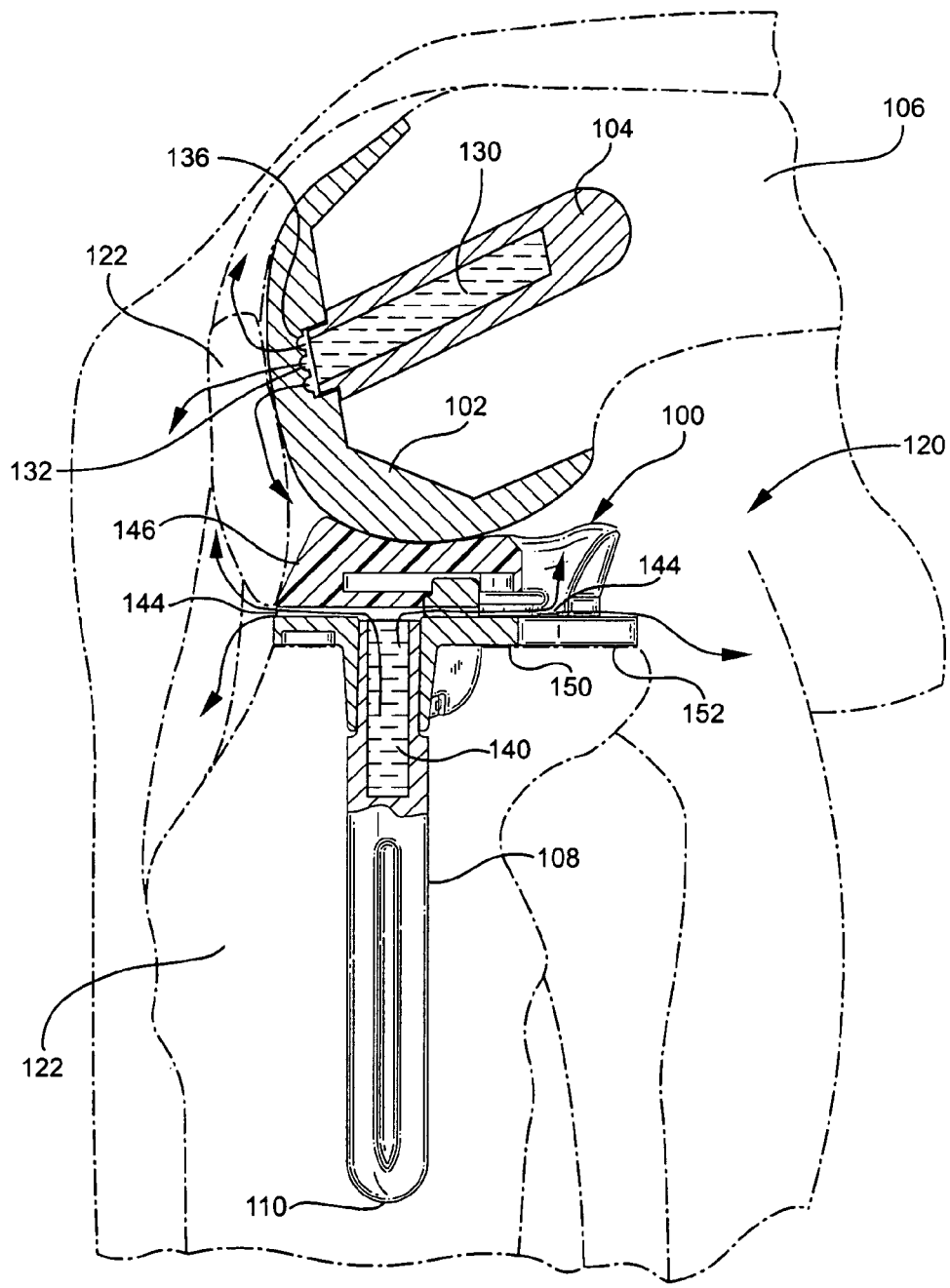
FIG. 7 is a cross-sectional view of the joint component shown in FIG. 6 showing the release of the therapeutic agent within the knee joint space.

Referring to FIG. 7, there is shown the cross-sectional view of the knee joint prosthesis 100 showing the analgesic or antibiotic being discharged into the joint cavity 120 via passageways 132 and 140.

Figure 8:
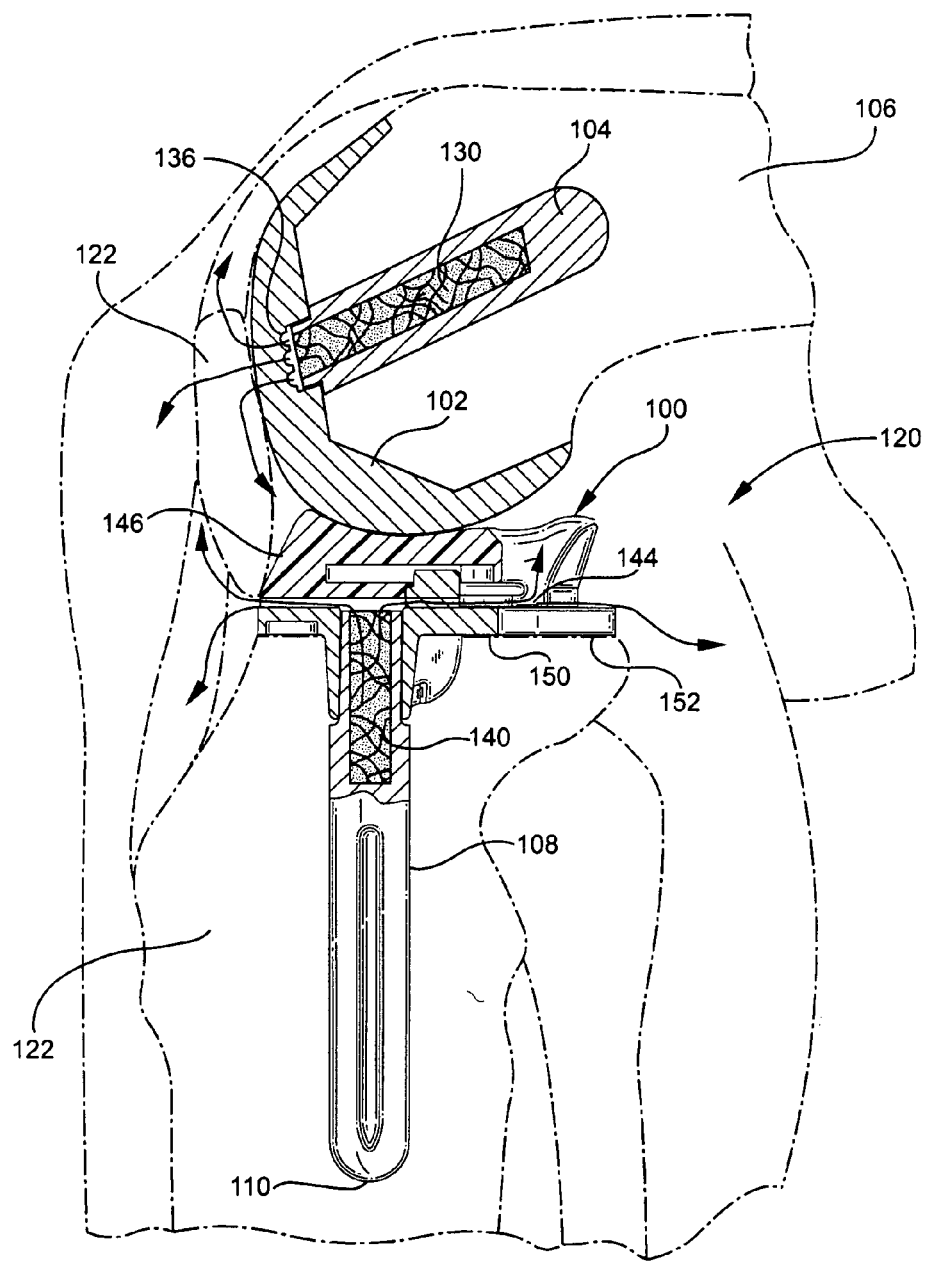
FIG. 8 is a cross-sectional view of the joint component of FIG. 6 showing the bioabsorbable/resorbable polymer partially resorbed by body fluids.

Referring to FIG. 8, there is shown the knee prosthesis 100 with the bioresorbable polymer partially resorbed. Referring to FIG. 6 there is shown an alternate embodiment for location of the polymer containing the antibiotic or analgesic or other therapeutic agent. In this embodiment, the polymer is molded around the outside of, for example, a tibial baseplate 150 such as at 152. The molded polymer including the therapeutic agent may extend several millimeters beyond the outer circumferential edge of the baseplate so that the therapeutic agent is released into the joint space as a result of the movement of the water component/body fluid into and out of the polymer.

The bioresorbable polymer also be attached to the implants as a film. In this case, the film may be bonded to the implant surfaces either with a glue such as the photo engravers glue used to bond the beads of U.S. Pat. No. 4,550,448 or the film itself may be made tacky by using processing parameters discussed herein below.

The process of making the bioabsorbable controlled drug release device of the present invention involves melting the polymer carrier in a special blending and grinding an extrusion device. The therapeutic agent such as bupivacaine purchased from Heumann Pharma GmbH in Germany is added in the blending and mixing step.

In the following examples, an Intelli-Torque Plasti-Corder® torque rheometer made by C. W. Brabender Instruments, Inc. of South Hackensack, N.J. was used. The instrument included a Prep-Mixer® with rollerblades, a quick loading shoot, a piston and 5 kilogram mass Granu-Grinder. The extrusion equipment was also obtained from Brabender and is the Intelli-Torque Plasti-Corder® ¾ inch/20/1/L/D single screw extruder with a single mixing zone screw, with a bin feed and a Flex-Lip ribbon dye of 20 mls., a strand dye with 5/16 inch nozzle insert and conveyor belt take off. The polymer used was a copolymer of poly-(DL-Lactide/Glyocolide) with a 53/47 mole ratio and with an inherent viscosity of 0.88 d/l/g. This material is purchased from Purac Biochem BV of The Netherlands. The material was supplied as granules in the 1-5 mm size range.

EXAMPLE I 180 grams of polymer was dry blended with 120 grams of bupivacaine purchased from Heumann Pharma GmbH Germany in a powder form. The polymer was supplied as granules in the 1-5 mm range (60% polymer/40% drug). The blend was put into a preheated Intelli-Torque Plasti-Corder® torque rheometer which was preheated to 150° C. and mixed for 8 minutes at 20 rpm. The homogenous blend produced is in the form of a homogenous polymeric matrix and was collected and, after cooling, was granulated using the Granu-Grinder to an average size of 3-5 mm. 150 grams of the granulated polymer/drug mixture was put into the Intelli-Torque Plasti-Corder® extruder with a 0.020 inch×2 inch dye and extruded at 121-157° C. as a 2 inch wide film of about 0.020 inch (0.54 mm) thick. The resulting film was given sample 557-4-3 and the release results shown in FIG. 9.

EXAMPLE II

The other half (150 grams) of the blend of Example I was extruded as a rod, using the same extruder but now fitted with a 5/16 inch diameter dye. Cylindrical samples of the polymer/drug matrix, which were very homogeneous, were obtained as sample 557-4-4 and the release results shown in FIG. 10.

Figure 11:
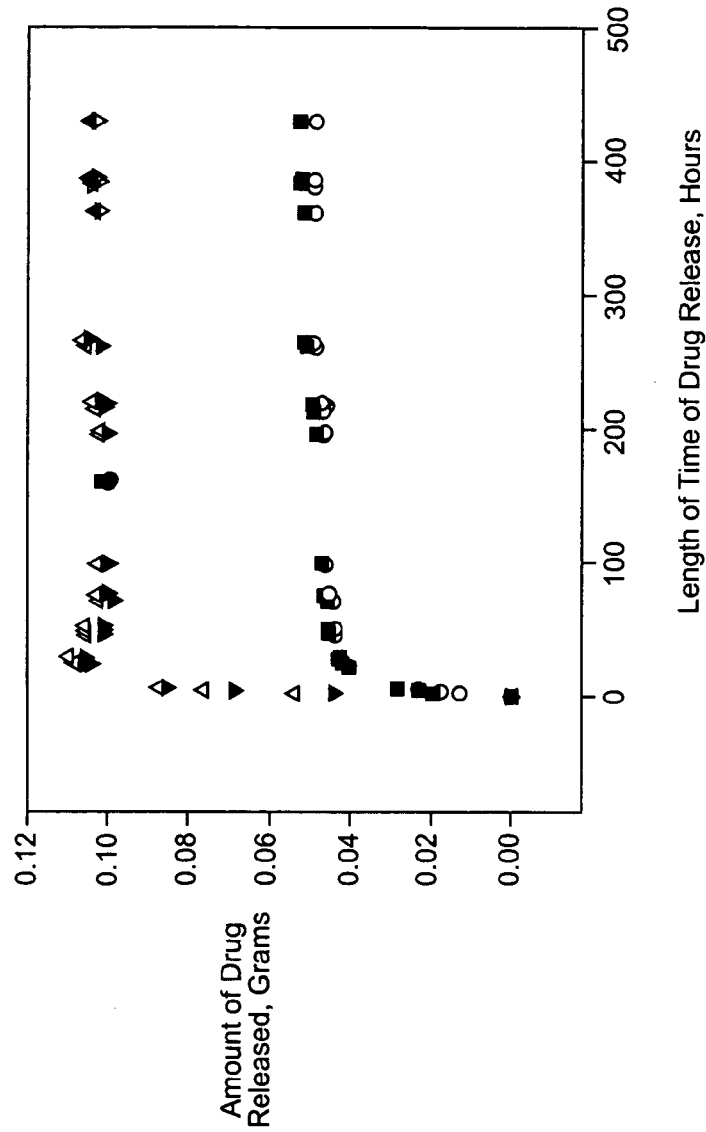
Figure 12:
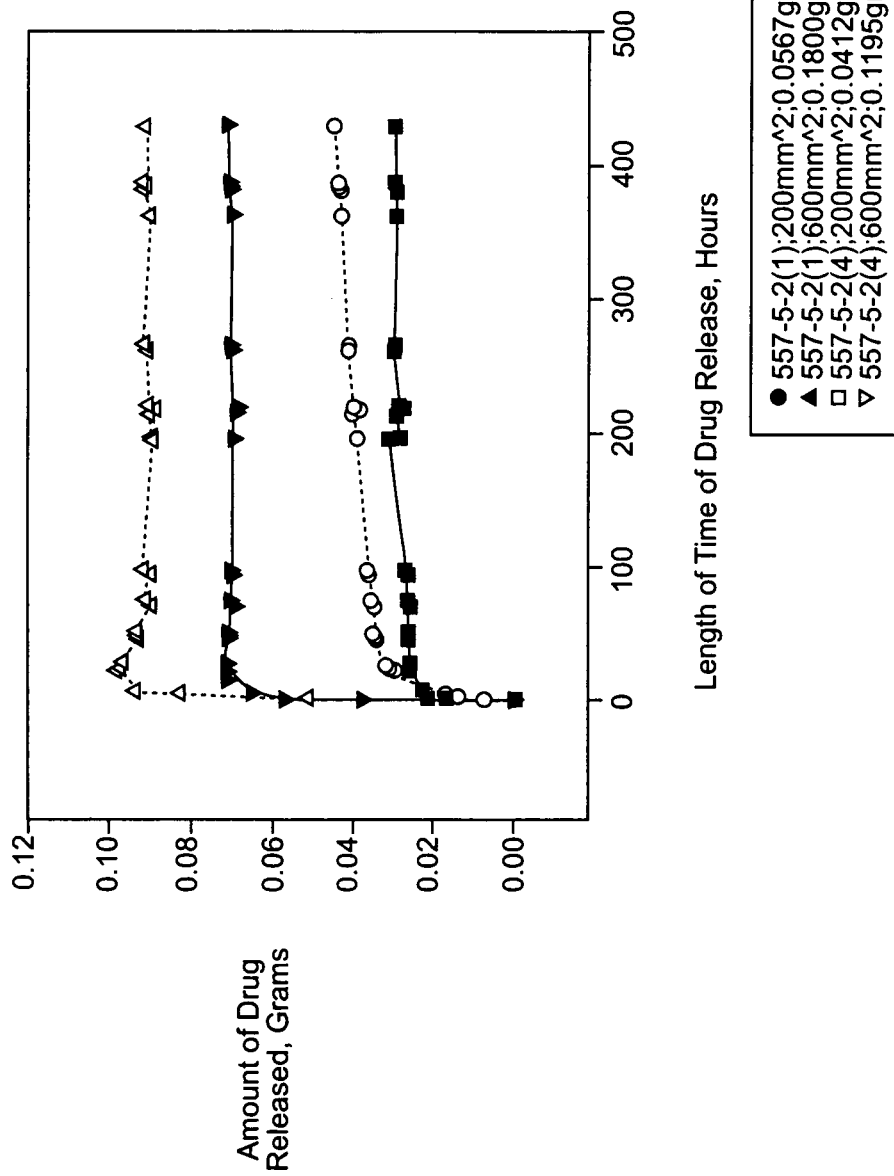

EXAMPLE III 120 grams of the copolymer were blended with 180 grams of bupivacaine (40% polymer/60% drug) in a dry state. The blend was put into the preheated-mixer which again was preheated to 150° C. Again, mixing continued for 8 minutes at 20 rpm. Other speeds and temperatures could be used if within the torque range of the machine. The homogeneous blend was then collected and, after cooling, was granulated using the Granu-Grinder into a size of 3-5 mm. 150 grams of the granulated polymer/drug was then put into the sheet extruder with the 0.020 inch by 2 inch dye and extruded at 121-157° C. to form a film of about 0.54 mm thick. One sheet was produced with this die setting as sample 557-5-1 being 0.54 mm thick. Then the die cap was changed to 0.013 inch and a film 0.35-0.47 mm thick identified as sample no. 557-5-2 was produced. The release results of these samples are shown in FIGS. 11 and 12 respectively.

EXAMPLE IV

Figure 13:
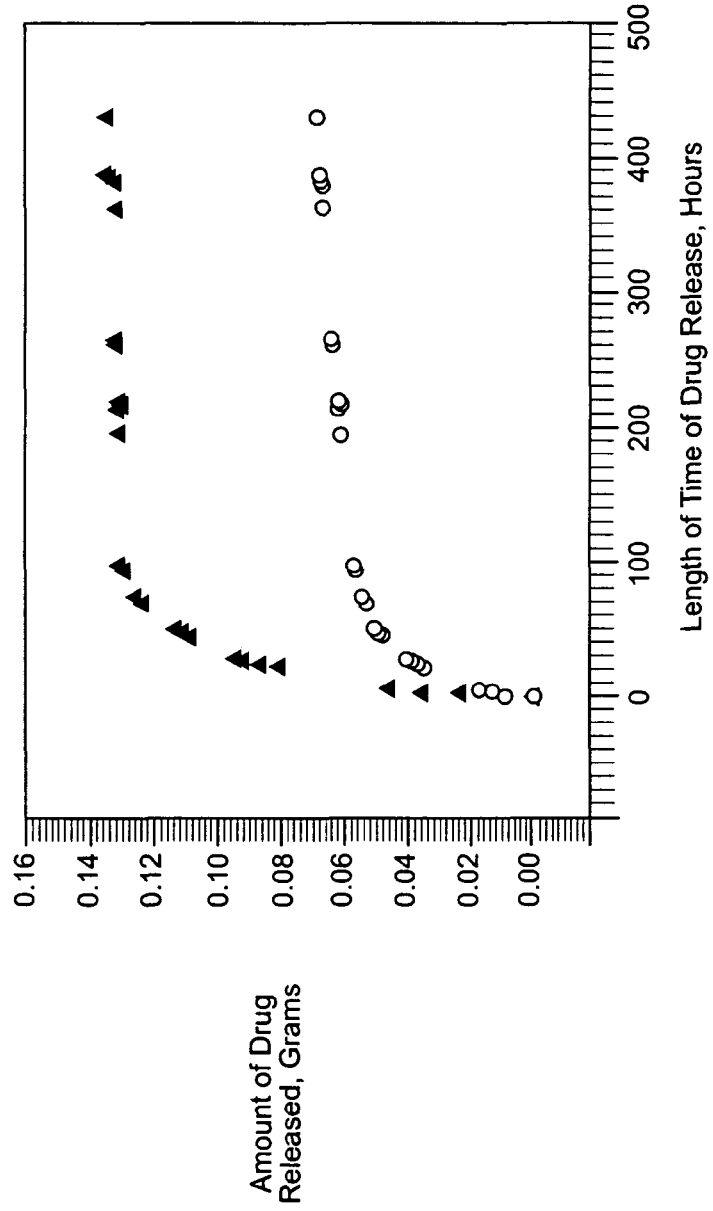

The other 150 grams of the blend was then extruded into a rod as in Example II with the Sample No. being 557-5-3 shown in FIG. 13.

Referring to FIGS. 9-12, the release rate of the bupivacaine from the sheets and rods made in Examples I-IV was determined by immersing a given weight of the device containing a given amount of drug in it into a specific volume of phosphate buffered saline (PBS) solution at a Ph of 7.4 and a temperature of 37° C. The sample was shaken in a vessel at 60 cycles per minute at a constant temperature in a planetary shaker bath. The amount of the drug which was released from the device as a function of time is determined at specified time by taking a sample of the outside solution and analyzing it by ultra-violet spectroscopy at 264 µm wave length.

Figure 9:
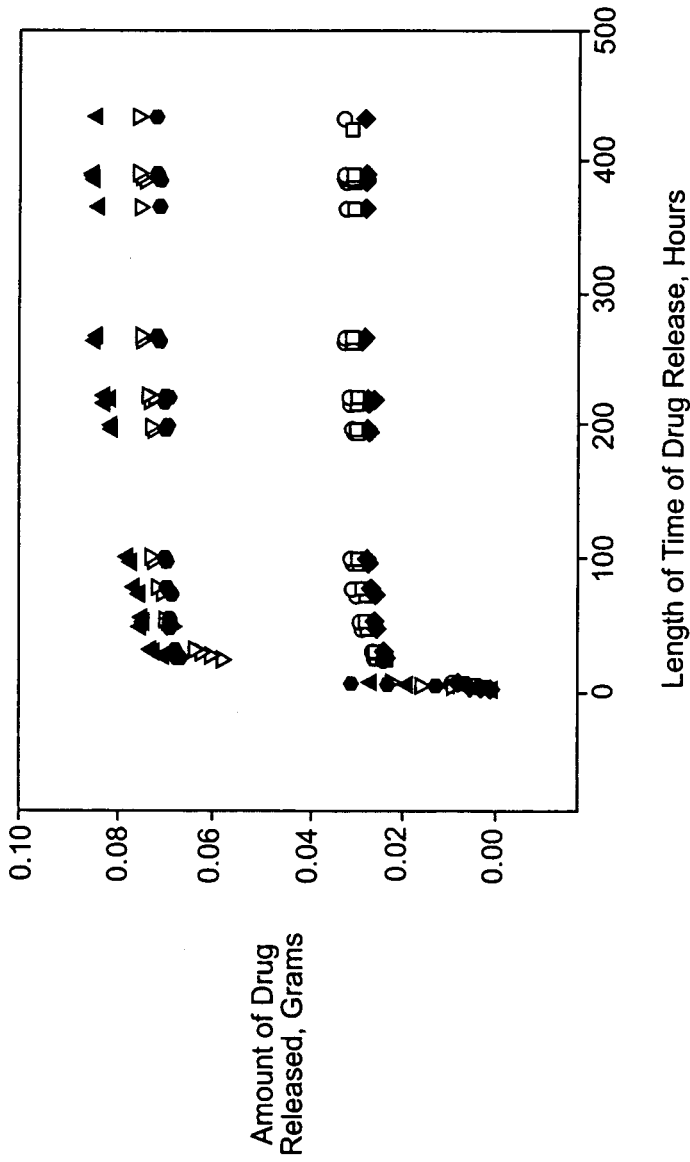
FIGS. 9-13 show the amount of bupivacaine released over a given length of time from sheets and rods of Examples I-IV.

FIG. 9 shows six samples of the films either 200 mm² surface area or 600 mm² surface area made in Example I. The rate of drug release is controlled by changing the weight and surface area of the device.

Figure 10:
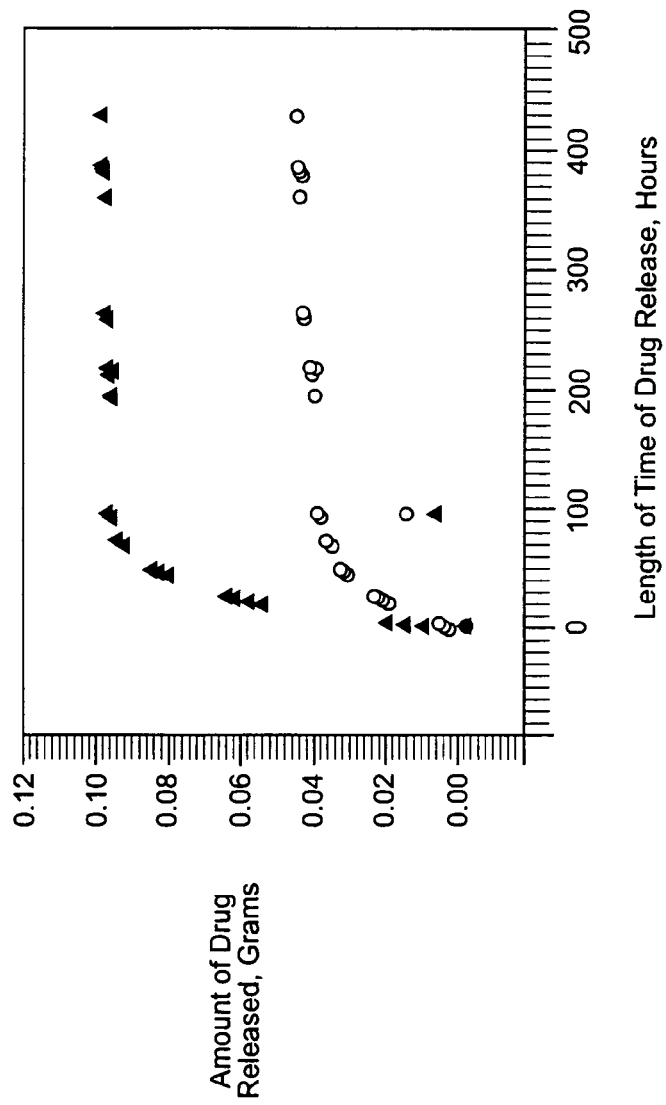

FIG. 10 shows the release rate of the bupivacaine from a 5/16 extruded rod made in accordance with Example II with one rod being 138.9 mm² surface area and 418.0 mm² surface area. The controlled release device can be a cylinder.

The rate of drug release can be controlled by changing the surface area and/or the weight of the device.

FIGS. 11 and 12 show the eight film samples made in Example III, with two of the samples being 200 mm² surface area and the other two being 600 mm² surface area. The rate of release of the drug is controlled by the weight and surface area of the device. Increasing the loading level of the drug from 40% in FIG. 9 to 60% in FIG. 11 increases the rate of drug release.

Likewise, referring to FIG. 13, the 5/16" rods of Example IV, one being 145.1 mm² surface area and the other being 432.5 mm² surface area are shown. Compared to FIG. 10, by increasing the level of drug loading, the rate and total amount of drug release was increased.

EXAMPLE V

A stock solution is prepared by dissolving 10.0 grams of terpolymer, Poly-(L-Lactide/D-Lactide/Glycolide), 85/5/10 molar ratio which has been previously injection molded, in 200 milliliters (mls.) dioxane.

Sample Preparation—42 grams. of this stock solution were added to 6.00 grams. of deionized water to obtain a 87/13 ratio of dioxane/water. The mixture was stirred and heated on a hot plate until clear solution was obtained. 0.5088 grams of bupivacaine was added to this and stored. This solution was frozen in dry-ice acetone for at least 2 hours. The frozen solution was freeze dried using VirTis freeze drier, Freeze mobile, model 3+SL for two days or until the vacuum level reaches the 44 milli-torr level at −57° C. This resulted in a porous foam. Foam sample No. 479-46-2 was obtained which weighed 2.4529 grams. Results of the study of release of bupivacaine from 0.2932 grams of the above device incubated in 50 mls. phosphate buffered saline at 37° C. is shown in FIG. 14.

EXAMPLE VI

The same procedure as used in Example V was followed except to make this device less porous the following amounts were used:
a) Ratio of Dioxane/Water 97/3;
b) Amount of water 1.237 grams;
c) Amount of bupivacaine 0.5052 grams; and
d) Weight of the device used 0.3082 grams.

Figure 14:
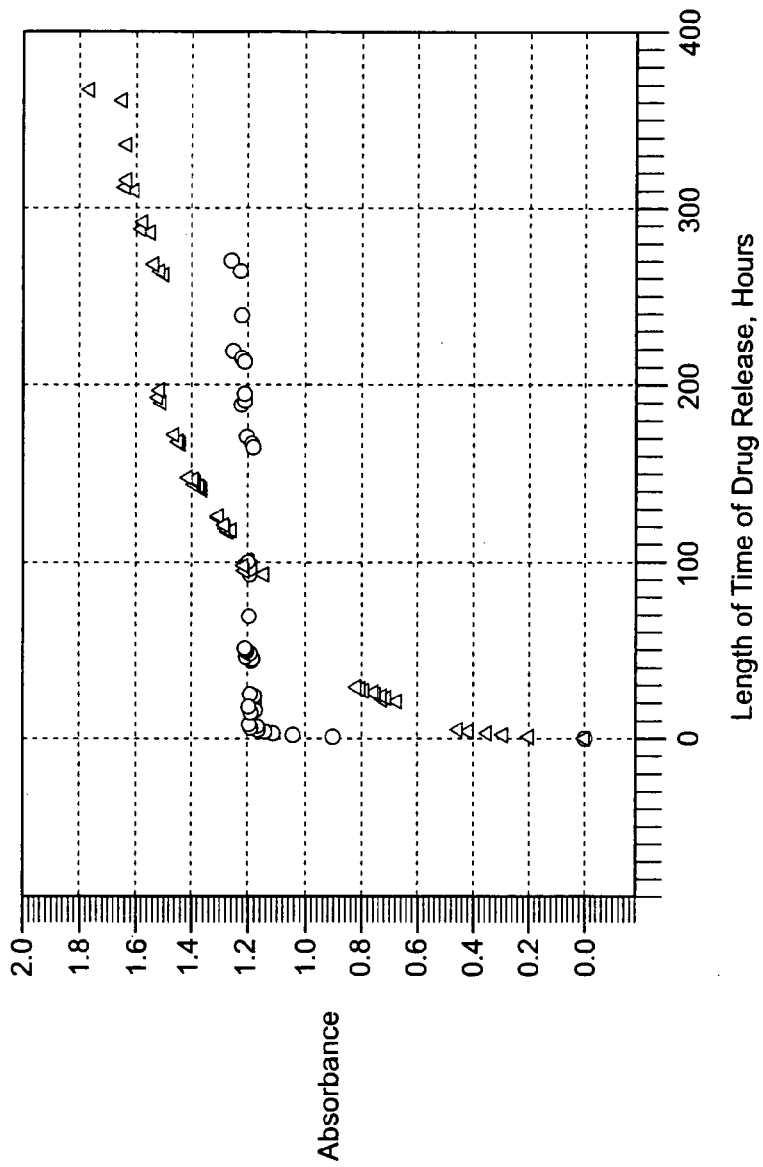
FIGS. 14-19 show the amount of bupivacaine released over a given length of time from sheets and rods of Examples V-XIX.

Results of the bupivacaine release from Examples VI sample 479-47-4 is also plotted in FIG. 14. This plot shows that by decreasing the amount of the water in the solvent/non-solvent mixture the structure is made less porous in Example VI and also the rate of release of bupivacaine was slowed.

EXAMPLE VII

This example and the following Example VIII illustrates the use of another polymer for making the controlled drug release device.

Sample preparation—22.5 grams of dioxane was added into a 250 ml beaker. 2.5 grams of a copolymer, poly-(DL Lactide/Glycolide) 50/50 mole ratio, was then added to the beaker and dissolved. 1.00 grams bupivacaine was added in the mixture and stirred. The mixture was frozen in dry-ice/acetone for two days. It was freeze-dried in the chamber of the freeze dryer as in Example V? The frozen mixture was dried under 100 μm vacuum for 24 hours. The porous structure produced was identified as number 479-87-1 and weight 3.1691 grams.

EXAMPLE VIII

Figure 15:
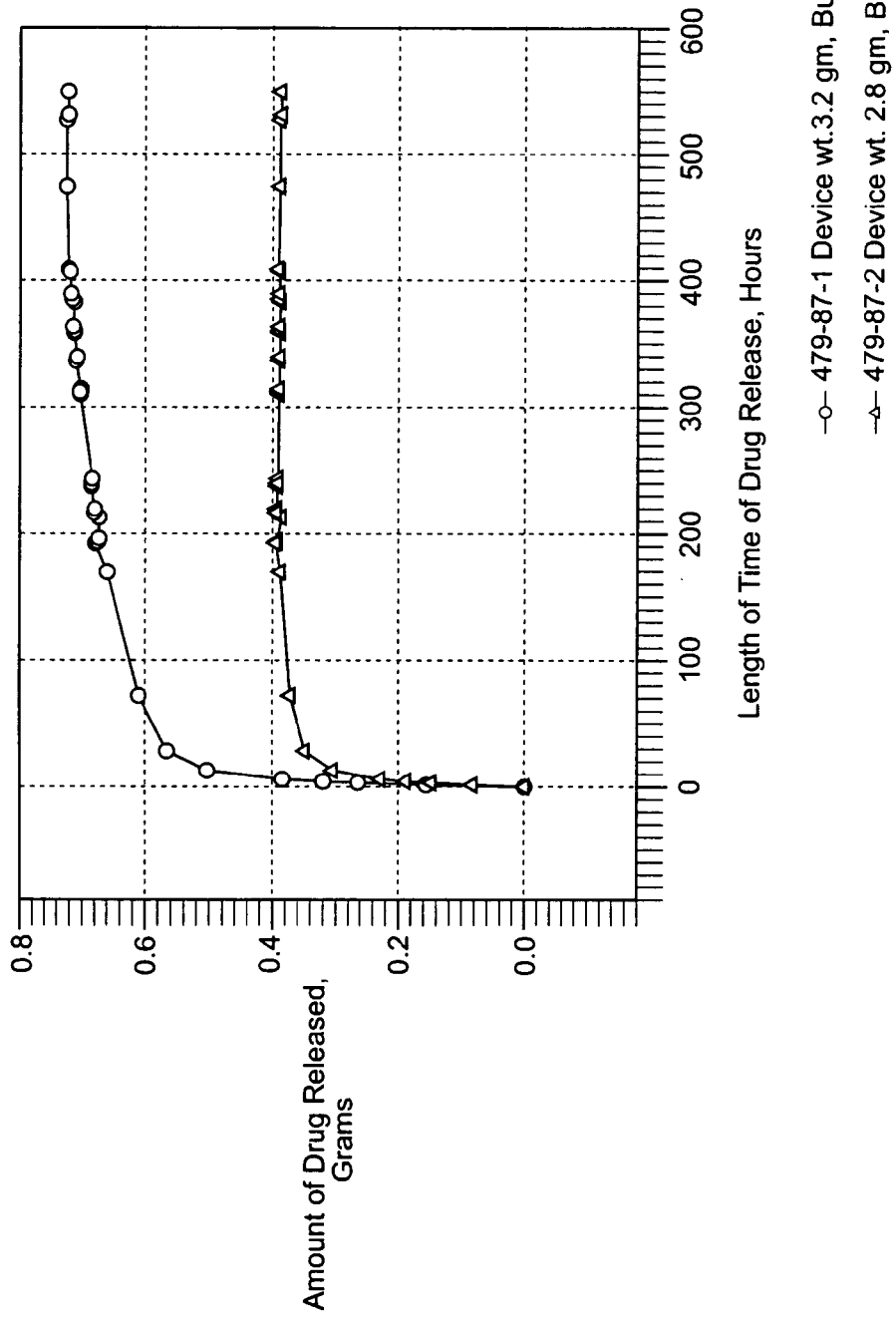

This sample was fabricated as in Example VII, except the weight of the bupivacaine was 0.500 grams and identified as sample 479-87-2. Results of the rate of release of bupivacaine from these two devices are plotted in FIG. 15, which shows that the rate of release can be adjusted to the desired levels within the range shown by changing the level of the drug loading in the device.

Table I characterizes the porosity of the samples produced by Examples V-VIII. The porous structure allows body fluids to dissolve and teach out the therapeutic agent.

TABLE I

Figure 20:
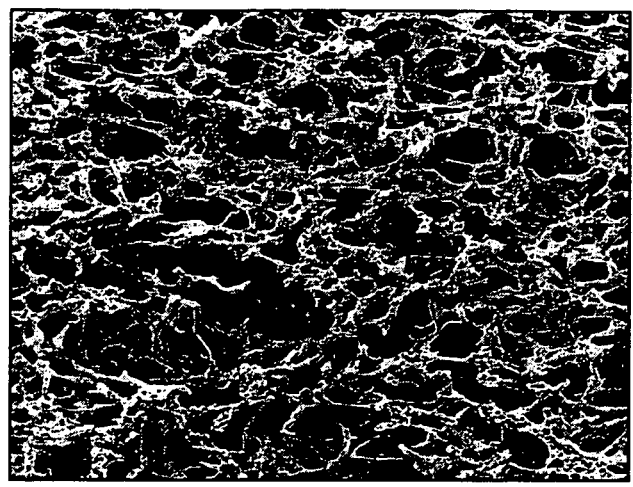
FIGS. 20, 21, 22 and 23 are photomicrographs of the samples produced in Examples V, VI, VII and VIII respectively, shown magnified at 200 power.
Figure 20A:
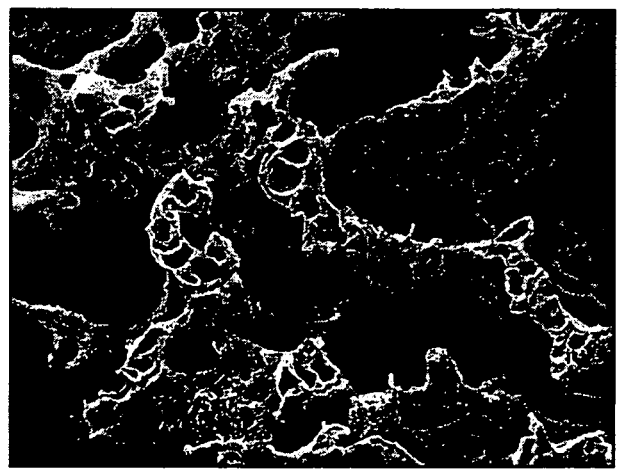
FIGS. 20a, 21a, 22a and 23a are photomicrographs of the samples produced in Examples V, VI, VII and VIII respectively, shown magnified at 1000 power.
Figure 21:
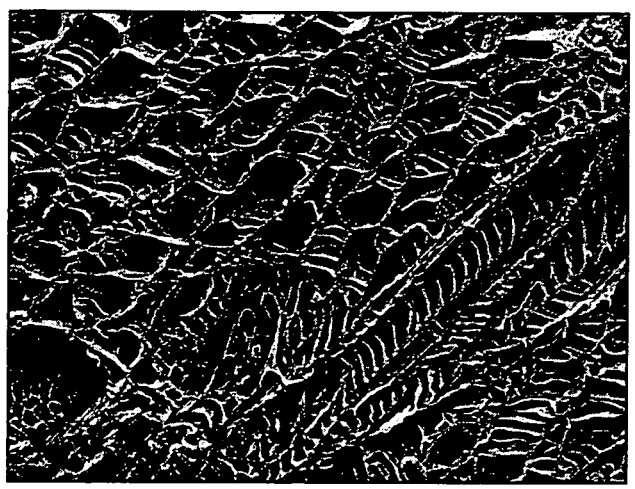
Figure 21A:
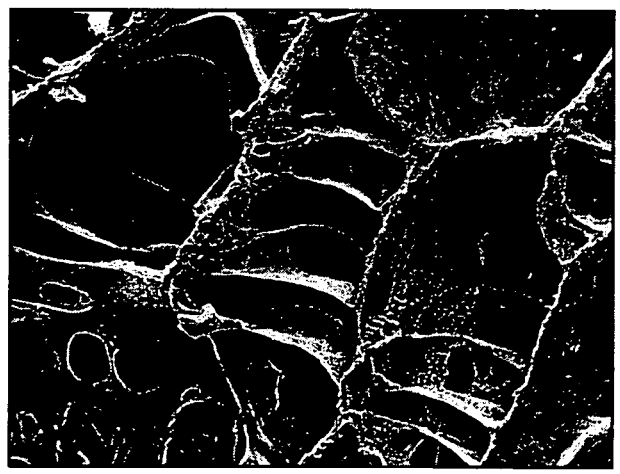
Figure 22:
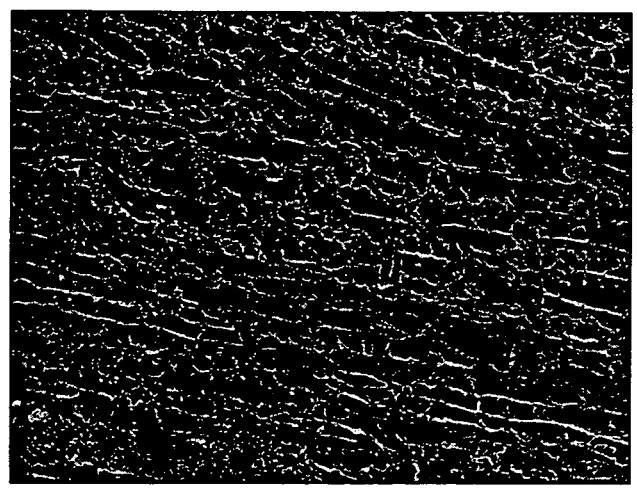
Figure 22A:
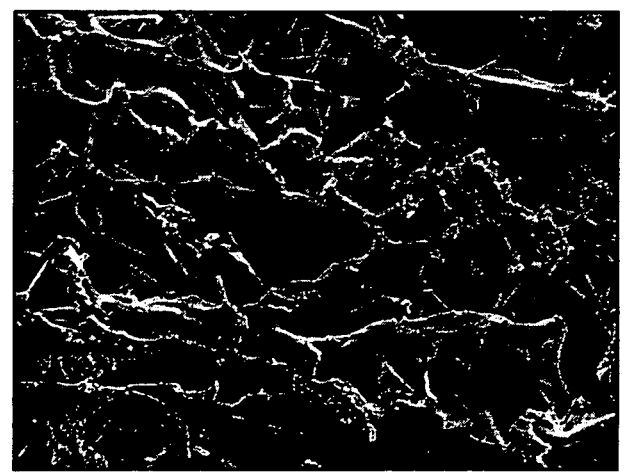
Figure 23:
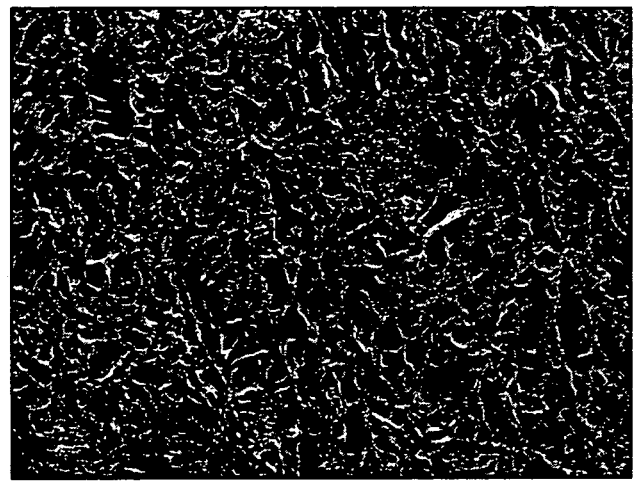
Figure 23A:
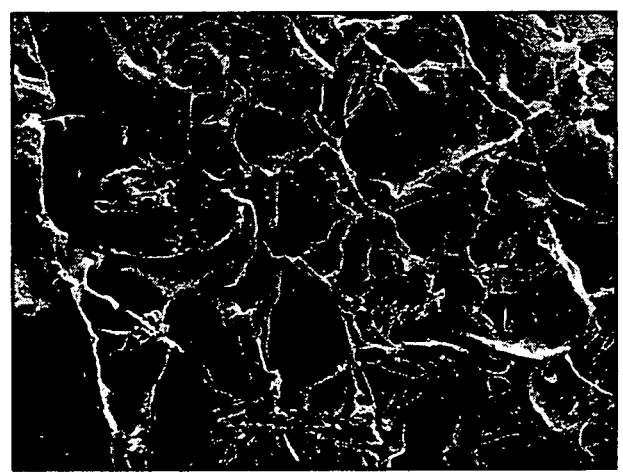

| | | | | POROSITY | | | |
|---|---|---|---|---|---|---|---|
| Example | Specimen | # Pores Counted | % Porosity | Av Pore Diameter (μm) | +/− std dev | min pore diameter (μm) | max pore diameter (μm) |
| V | 479-46-1 (FIG. 20) | 925 | 39.7 | 8.5 | 9.8 | 2.2 | 120.9 |
| VI | 479-47-4 (FIG. 21) | 543 | 29.8 | 12.0 | 7.7 | 5.0 | 70.6 |
| VII | 479-87-1 (FIG. 22) | 666 | 30.0 | 10.0 | 8.2 | 4.0 | 77.3 |
| VIII | 479-87-2 (FIG. 23) | 445 | 25.3 | 11.8 | 6.2 | 6.0 | 45.1 |

Solvent Casting—Reservoir film devices fabricated by a solvent casting method are illustrated by the following examples. The first two examples illustrate the effect of the solvent used on the rate of release and the second two examples (IX and X) illustrate the effect of drug loading or the amount of the drug in the matrix on the rate of release of the drug.

EXAMPLE IX 2 grams of the copolymer, poly-(DL-Lactide/Glycolide), 50/50 mole ratio, were dissolved in 26 grams of dioxane. Then 2 grams of bupivacaine was added and the suspension stirred and cast on Teflon coated tray. The tray was allowed to dry under a hood for two days and then the film, which was formed, was removed from the tray and dried under vacuum of 240 μm (microns) mercury. This film was homogeneous and flexible and it weighed 3.7489 grams. This was identified as sample number 479-74-1. This film was cut into strips and all the strips were immersed in 200 mls phosphate buffered saline (PBS) at a pH of 7.4 and at a temperature of 37° C. and put on a constant temperature shaker set at 37°

C. and 60 Hz. to determine the rate of release of the drug from the device. Results of the drug release study are plotted in FIG. 16.

EXAMPLE X

A film was made in a similar way to that of Example IX, except for the following:
a) The solvent used was 36 grams of chloroform;
b) The film obtained was brittle and it weight 3.4907 grams; and
c) It was given identification number 479-74-2.

Figure 16:
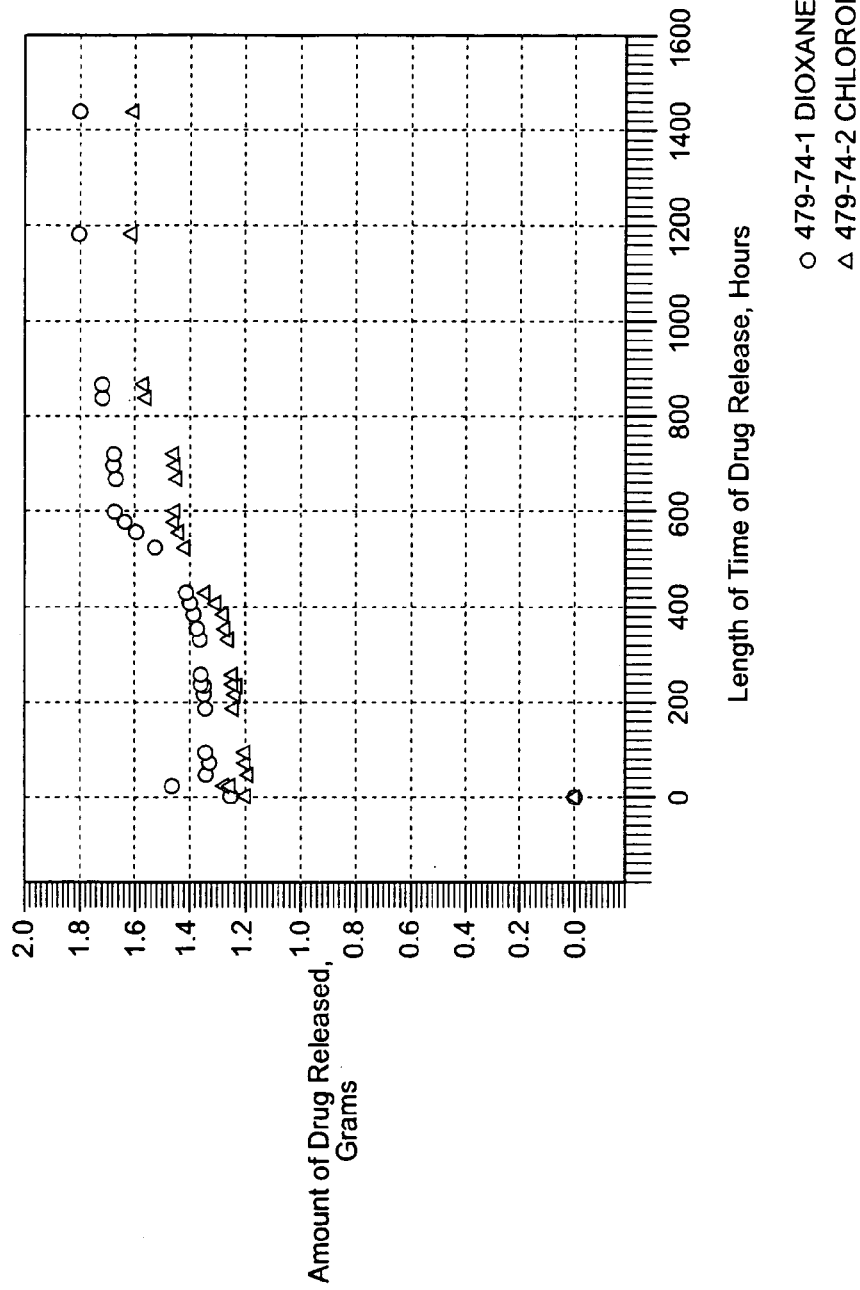

Results of the drug release study with this film matrix is plotted in FIG. 16 also. This data indicates that dioxane is the preferred solvent because it gives a more homogeneous and a more flexible film. The initial rate of drug release was very fast when either solvent is used and that a somewhat higher rate was obtained with the dioxane based matrix.

EXAMPLE XI

Example XI illustrates the fabrication of the film matrix which is loaded to a lower extent with the drug. 5 grams copolymer, poly-(DL-Lactide/Glycolide), 50/50 mole ratio was dissolved in 45 grams dioxane. 1.00 grams of bupivacaine was added and the mixture stirred. The suspension was cast on a Teflon coated tray and dried under a hood and then under a vacuum of 240 µm mercury. The homogeneous film matrix produced was identified as 479-86-1.

Figure 17:
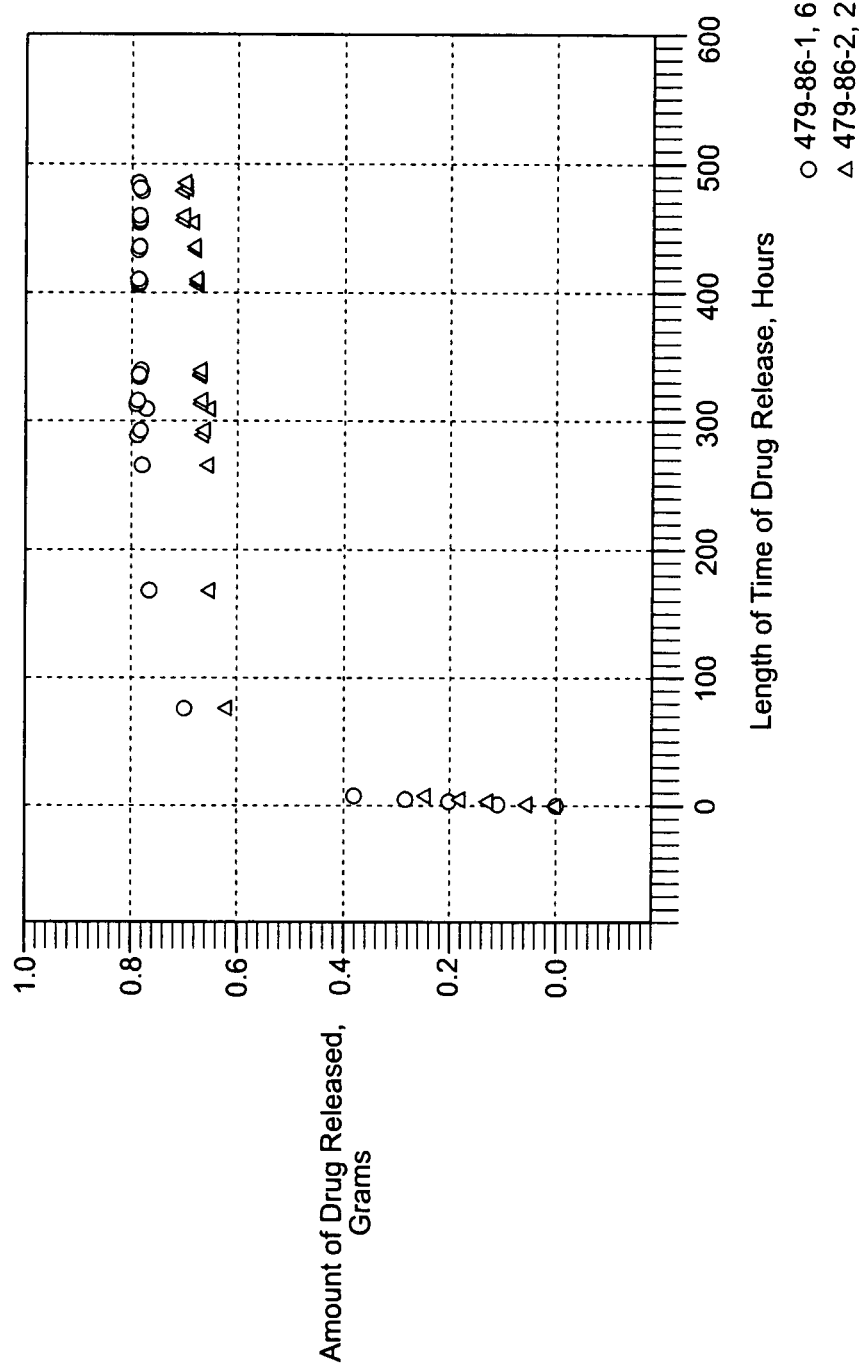

Results of the drug release study utilizing 6.0 grams of the matrix film are plotted in FIG. 17.

EXAMPLE XII

Example XII illustrates that the matrix film can be loaded to a higher level and a smaller amount of the matrix film would be required to be used in this case to still deliver large amounts of the drug. The fabrication of the film matrix of this example is different from Example XI only in that the amount of the bupivacaine added was 3.00 grams and this sample was identified as device 479-86-2. The results of the drug release study with this sample are plotted in FIG. 17.

Pouch Type Devices—These devices are constructed from the solvent cast films by heat-sealing the edges or by gluing the edges with the polymer solution. The drug was put in them either as powder or as a film matrix containing the drug.

Figure 18:
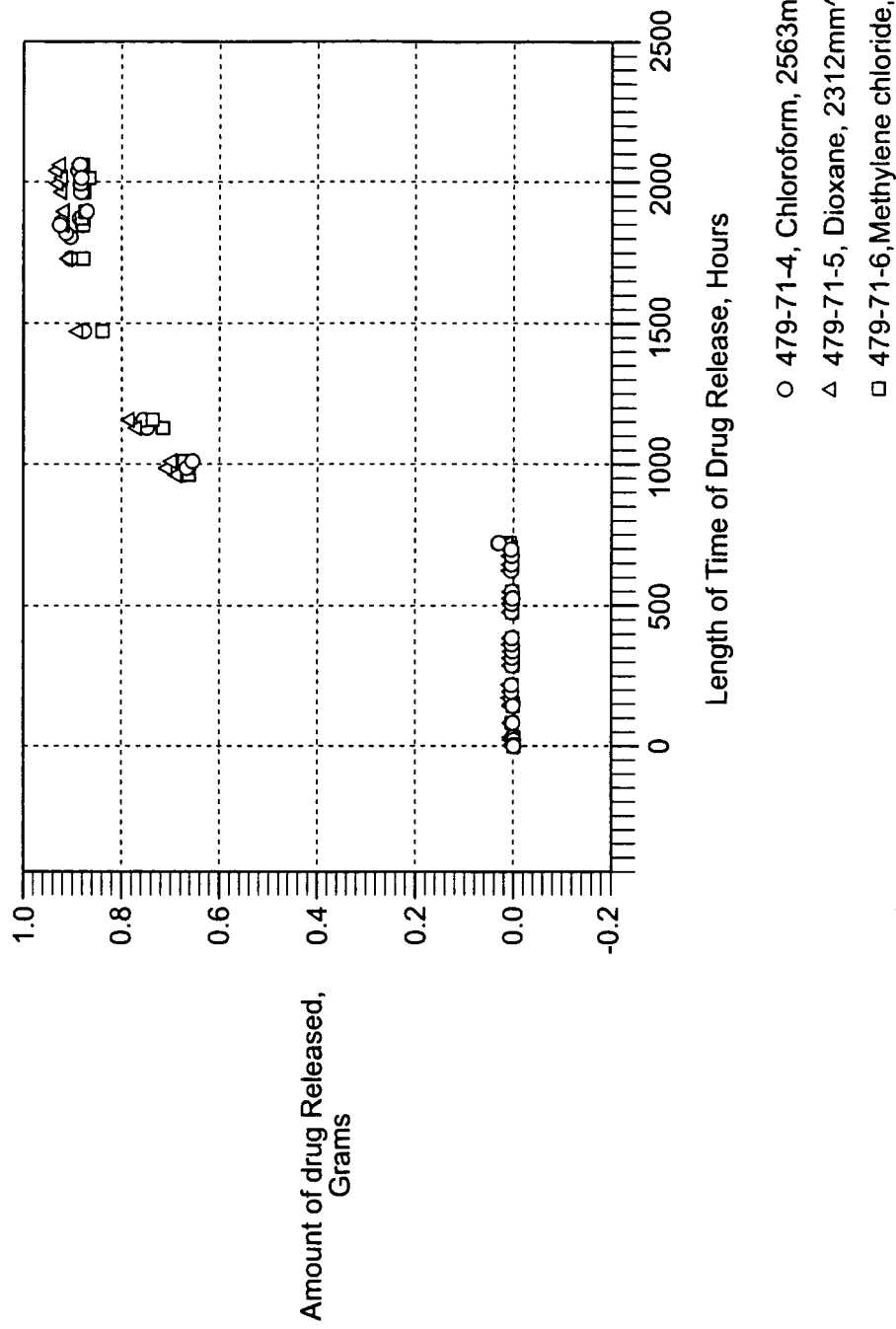

EXAMPLE XIII 1 gram of the copolymer, poly-(DL-Lactide/Glycolide), 50/50 molar, ratio was dissolved in 99 mls. of chloroform. This solution was cast on a 6"×10" Teflon coated tray. This was dried at room temperature for two days and then dried under 240 µm-Hg vacuum for a day. A rectangular piece of about 36 mm×72 mm was cut from this film to form a pouch. This was folded to form a square of about 36 mm×36 mm square. Three edges of the pouch were heat sealed using a conventional heat sealer. 1 gram of bupivacaine powder was put into this pouch and the fourth edge heat-sealed. This was identified as sample number 479-71-4. This pouch was immersed in 150 mls of phosphate buffered saline at 37° C. and was put in a constant temperature shaker bath set at 60 Hz. Samples of the outside solution were analyzed by U.V. Spectrophotometry at various times and the amount of the drug released by the pouch were determined. Results are plotted in FIG. 18 along with the results from Examples XIV and XV.

EXAMPLE XIV

This example was similar to Example XIII except that the solvent was dioxane and the film, which formed, was very sticky and was indicated as sample 479-71-5. Therefore the edges were just pressed together at room temperature and sealed this way. It was determined that the film so produced was sticky enough to adhere to metal or plastic implants.

EXAMPLE XV

This experiment was carried out as in Example XIII, however, the solvent used was methylenechloride and indicated as sample 479-71-6. The results shown in FIG. 18 suggest that the release of the drug from these devices does not start until after about 700 hours of incubation. This delay would be useful when a lag time for the start of the drug release is needed. Furthermore, these results also suggest that the rate of drug release is not affected significantly by changing the solvent used in the process of fabrication of the films forming these devices.

Coated Devices—Another way of controlling the rate of the drug release from a device is illustrated in the examples below.

EXAMPLE XVI 120 grams of polymer, poly-(DL-Lactide/Glycolide), 50/50 mole ratio, was dry blended and melt blended with 180 grams of bupivacaine, using Brabender mixer as in Examples I-IV. The extrudate was ground. The ground material was extruded into rods of diameter 7.86 mm. A cylinder having a length of 21.2 mm was cut. The cylinder has a surface area of 621.6 mm$^2$ and weighed 1.1980 grams. The cylinder had 60% drug in it by weight.

This sample is identified as 557-13-5 and was incubated in 500 mls of PBS in a 37° C. constant temperature shaker bath at 60 Hz. The rate of drug released from this device was plotted in FIG. 19.

EXAMPLE XVII 120 grams of polymer, poly-(DL-Lactide/Glycolide), 50/50 mole ratio, was dry blended with 180 grams of bupivacaine and melt blended, using Brabender mixer. The extrudate was ground to a particle size of 3-5 mm. The ground material was melted and extruded into rods of diameter 7.87 mm. A cylinder having a length of 21.3 mm cylinder was cut. The rod had a surface area of 622.9 mm$^2$ and weighed 1.200 grams. Again, the rod had 60% drug in it by weight. The above cylindrical rod was coated with a 5% solution of poly-(DL-Lactide/Glycolide), 50/50 ratio in dioxane by immersing the device in this solution and then air-drying it in a hood. The coated device was vacuum dried at 200 µm Hg for 3 days.

Figure 19:
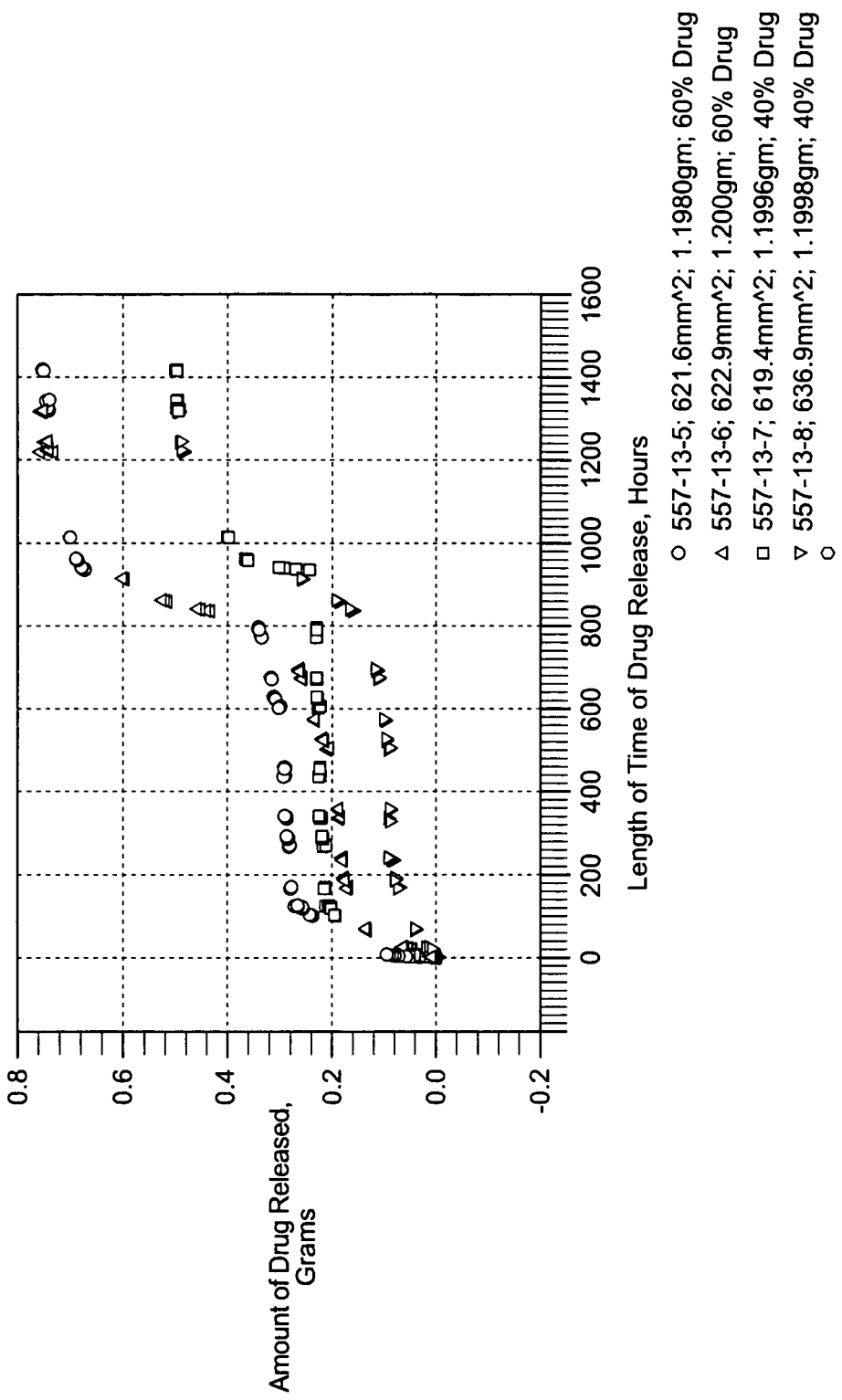

This sample was identified as 557-13-6 and it was tested for drug release as Example XVI and the results are plotted in FIG. 19.

EXAMPLE XVIII 180 grams of polymer, poly-(DL-Lactide/Glycolide), 50/50 mole ratio, were dry blended and then melt blended with 120 grams of bupivacaine, using Brabender mixer. The extrudate from the mixer was ground to a particle size of 3-5 mm. The ground material was remelted and extruded into cylindrical rods of diameter 7.78 mm which were cut to a length of 21.45 mm having a surface area of 619.4 mm$^2$ and a weight of 1.1996 grams. This rod had 40% drug in it by weight. This sample was identified as 557-13-7 and it was tested for drug release as in Example XVI. The results were also plotted in FIG. 19.

EXAMPLE XIX 180 grams of polymer, poly-(DL-Lactide/Glycolide), 50/50 mole ratio, was dry blended with 120 grams of bupivacaine and then melt blended, using a Brabender mixer. The extrudate was ground as above and the ground material was extruded into rods having a diameter of 7.31 mm. A length of 24.08 mm was cut from the cylinder which cut rod had a surface area of 636.9 mm$^2$ and weighed of 1.1998 grams. This rod also had 40% drug in it by weight. This cylindrical device was coated with a 5% solution of poly-(DL-Lactide/Glycolide), 50/50 ratio in dioxane by immersing the device in this solution and then air-drying it in a hood. The coated device was vacuum dried at 200 μm Hg for 3 days. This sample was identified as 557-13-8 and it was tested for drug release as in Example XVI. The results were also plotted in FIG. 19.

These last four examples illustrate that the rate of drug release can be controlled from a loaded polymeric cylinder by applying a polymeric coating to the device. Furthermore, the rate of drug release can be controlled by changing the level of drug loading in the device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic joint implant device for releasing a therapeutic agent into a joint space comprising:
   (a) a stem component for insertion into a bone, contiguous with
   (b) a joint component for extension into a fluid-containing joint space; and
   (c) a cavity enclosed within the stem and joint components that (i) extends from the stem component into the joint component, having an opening in the joint component and (ii) serves as a reservoir, containing a bioresorbable polymer comprising a therapeutic agent selected from the group consisting of an analgesic, an antibiotic, and a combination thereof;
   wherein the device is configured such that, when at its intended location in a subject, the opening of the reservoir is at a position in the joint component that extends beyond the bone and into the joint space, such that the opening allows joint fluid to diffuse into the device, providing sustained release of agent.

2. The device of claim 1, wherein the amount of therapeutic agent in the bioresorbable polymer is between 40 and 60 percent.

3. The device of claim 1, wherein the bioresorbable polymer is poly-(DL Lactide/Gylcolide co-polymer.

4. The device of claim 1, wherein the therapeutic agent comprises an analgesic selected from the group consisting of bupivacaine, ropivacaine, dibucaine, etidocaine, tetracaine, lidocaine, and combinations thereof.

5. The device of claim 3, wherein the therapeutic agent comprises an analgesic selected from the group consisting of bupivacaine, ropivacaine, dibucaine, etidocaine, tetracaine, lidocaine, and combinations thereof.

6. The device of claim 4, wherein the therapeutic agent comprises bupivacaine.

7. The device of claim 5, wherein the therapeutic agent comprises bupivacaine.

8. The device of claim 4, wherein the therapeutic agent further comprises an antibiotic.

9. The device of claim 5, wherein the therapeutic agent further comprises an antibiotic.

10. A prosthetic joint implant device for releasing a therapeutic agent into a hip joint space comprising:
    (a) a stem component for insertion into a femur, contiguous with
    (b) a joint component for extension into a fluid-containing hip joint space, continuous with a prosthetic femoral head; and
    (c) a cavity enclosed within the stem and joint components that (i) extends from the stem component into the joint component, having an opening in the joint component and (ii) serves as a reservoir, containing a bioresorbable polymer comprising a therapeutic agent selected from the group consisting of an analgesic, an antibiotic, and a combination thereof;
    wherein the device is configured such that, when at its intended location in a subject, the opening of the reservoir is at a position in the joint component that extends beyond the bone and into the joint space, such that the opening allows joint fluid to diffuse into the device, providing sustained release of agent.

11. The device of claim 10, wherein the amount of therapeutic agent in the bioresorbable polymer is between 40 and 60 percent.

12. The device of claim 10, wherein the bioresorbable polymer is poly-(DL Lactide/Gylcolide co-polymer.

13. The device of claim 10, wherein the therapeutic agent comprises an analgesic selected from the group consisting of bupivacaine, ropivacaine, dibucaine, etidocaine, tetracaine, lidocaine, and combinations thereof.

14. The device of claim 10, wherein the therapeutic agent comprises bupivacaine.

15. The device of claim 13, wherein the therapeutic agent further comprises an antibiotic.

16. A prosthetic joint implant device for releasing a therapeutic agent into a knee joint space comprising:
    (a) a stem component for insertion into a femur or tibia, contiguous with
    (b) a joint component for extension into a fluid-containing knee joint space; and
    (c) a cavity enclosed within the stem and joint components that (i) extends from the stem component into the joint component, having an opening in the joint component and (ii) serves as a reservoir, containing a bioresorbable polymer comprising a therapeutic agent selected from the group consisting of an analgesic, an antibiotic, and a combination thereof;
    wherein the device is configured such that, when at its intended location in a subject, the opening of the reservoir is at a position in the joint component that extends beyond the bone and into the joint space, such that the opening allows joint fluid to diffuse into the device, providing sustained release of agent.

17. The device of claim 16, wherein the amount of therapeutic agent in the bioresorbable polymer is between 40 and 60 percent.

18. The device of claim 16, wherein the bioresorbable polymer is poly-(DL Lactide/Gylcolide co-polymer.

19. The device of claim 16, wherein the therapeutic agent comprises an analgesic selected from the group consisting of bupivacaine, ropivacaine, dibucaine, etidocaine, tetracaine, lidocaine, and combinations thereof.

20. The device of claim 16, wherein the therapeutic agent comprises bupivacaine.

21. The device of claim 19, wherein the therapeutic agent further comprises an antibiotic.

22. A method for supplying a therapeutic agent to a joint space of a subject recipient of a joint implant, comprising:
  (i) introducing, into the joint of a subject in need of such treatment, a joint implant device comprising:
  (a) a stem component for insertion into a bone, contiguous with
  (b) a joint component for extension into a fluid-containing joint space; and
  (c) a cavity enclosed within the stem and joint components that (i) extends from the stem component into the joint component, having an opening in the joint component and (ii) serves as a reservoir, containing a bioresorbable polymer comprising a therapeutic agent selected from the group consisting of an analgesic, an antibiotic, and a combination thereof, and
  (ii) positioning the stem component in the bone such that the opening of the reservoir is located beyond the bone within the joint space, such that the opening allows joint fluid to diffuse into the device and provides sustained release of therapeutic agent.

23. The method of claim 22, wherein the joint is a hip joint.

24. The method of claim 22, wherein the joint is a knee joint.

25. The method of claim 22, wherein the amount of therapeutic agent in the bioresorbable polymer is between 40 and 60 percent.

26. The method of claim 22, wherein the bioresorbable polymer is poly-(DL Lactide/Gylcolide co-polymer.

27. The method of claim 22, wherein the therapeutic agent comprises an analgesic selected from the group consisting of bupivacaine, ropivacaine, dibucaine, etidocaine, tetracaine, lidocaine, and combinations thereof.

28. The method of claim 22, wherein the therapeutic agent comprises bupivacaine.

29. The method of claim 27, wherein the therapeutic agent further comprises an antibiotic.

30. The device of claim 1, further comprising a coating around non-load bearing surfaces of the device that extend into or are exposed to the joint space, said coating comprising a therapeutic agent selected from the group consisting of an analgesic, an antibiotic, and a combination thereof.

31. The device of claim 10, further comprising a coating around non-load bearing surfaces of the device that extend into or are exposed to the joint space, said coating comprising a therapeutic agent selected from the group consisting of an analgesic, an antibiotic, and a combination thereof.

32. The device of claim 16, further comprising a coating around non-load bearing surfaces of the device that extend into or are exposed to the joint space, said coating comprising a therapeutic agent selected from the group consisting of an analgesic, an antibiotic, and a combination thereof.

33. The device of claim 16, further comprising a tibial baseplate and a bioresorbable polymer around the outside of said tibial baseplate, where the bioresorbable polymer around said baseplate comprises a therapeutic agent selected from the group consisting of an analgesic, an antibiotic, and a combination thereof.

34. The method of claim 22 wherein the device further comprises a coating around non-load bearing surfaces of the device that extend into or are exposed to the joint space, said coating comprising a therapeutic agent selected from the group consisting of an analgesic, an antibiotic, and a combination thereof.

35. The method of claim 23 wherein the device further comprises a coating around non-load bearing surfaces of the device that extend into or are exposed to the joint space, said coating comprising a therapeutic agent selected from the group consisting of an analgesic, an antibiotic, and a combination thereof.

36. The method of claim 24 wherein the device further comprises a coating around non-load bearing surfaces of the device that extend into or are exposed to the joint space, said coating comprising a therapeutic agent selected from the group consisting of an analgesic, an antibiotic, and a combination thereof.

37. The method of claim 24 wherein the device further comprises a tibial baseplate and a bioresorbable polymer around the outside of said tibial baseplate, where the bioresorbable polymer around said baseplate comprises a therapeutic agent selected from the group consisting of an analgesic, an antibiotic, and a combination thereof.

* * * * *